US008852085B2

(12) United States Patent
Shener-Irmakoglu et al.

(10) Patent No.: US 8,852,085 B2
(45) Date of Patent: *Oct. 7, 2014

(54) TISSUE RESECTING SYSTEM

(71) Applicant: Smith & Nephew, Inc., Memphis, TN (US)

(72) Inventors: Cemal Shener-Irmakoglu, Woburn, MA (US); Christopher R. Newell, Haverhill, MA (US); Petter Hedstrom, Haverhill, MA (US); Kenneth W. Krause, Sandown, NH (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/860,654

(22) Filed: Apr. 11, 2013

(65) Prior Publication Data

US 2013/0225928 A1    Aug. 29, 2013

Related U.S. Application Data

(63) Continuation of application No. 13/212,240, filed on Aug. 18, 2011, now Pat. No. 8,419,626, which is a continuation of application No. 10/927,244, filed on Aug. 27, 2004, now Pat. No. 8,062,214.

(51) Int. Cl.
| | |
|---|---|
| *A61B 1/12* | (2006.01) |
| *A61B 1/015* | (2006.01) |
| *A61B 1/018* | (2006.01) |
| *A61B 1/00* | (2006.01) |
| *A61B 17/32* | (2006.01) |
| *A61B 17/34* | (2006.01) |

(52) U.S. Cl.
CPC .............. *A61B 1/015* (2013.01); *A61B 1/018* (2013.01); *A61B 2017/320024* (2013.01); *A61B 17/3498* (2013.01); *A61B 1/00068* (2013.01); *A61B 2017/3445* (2013.01); *A61B 17/3421* (2013.01)

USPC ........... 600/159; 600/105; 600/153; 600/156; 600/158

(58) Field of Classification Search
USPC ........................... 600/105, 159; 604/246–249
See application file for complete search history.

(56) References Cited

U.S. PATENT DOCUMENTS

| 1,666,332 A | 4/1928 | Hirsch |
| 2,708,437 A | 5/1955 | Hutchins |

(Continued)

FOREIGN PATENT DOCUMENTS

| DE | 3206381 | 9/1983 |
| DE | 3339322 | 5/1984 |

(Continued)

OTHER PUBLICATIONS

Office Action for corresponding Japanese Application No. 2007-530014, in English, mailed Feb. 15, 2011, 10 pages.

(Continued)

*Primary Examiner* — Matthew J Kasztejna
(74) *Attorney, Agent, or Firm* — Nixon Peabody LLP

(57) ABSTRACT

A surgical system includes a first instrument defining a first channel and a second instrument receivable by the first channel. The second instrument defines a second channel. A valve coupled to the first instrument controls fluid flow through the first channel, such that impedance of fluid flow through the first channel is substantially the same without the second instrument received in the first channel and with the first channel partially blocked by the second instrument. In another aspect, a surgical apparatus includes an outer member and an inner member received within the outer member to define a first channel therebetween. The inner member houses an optical lens and defines a second channel for receiving a surgical instrument. The first and second channels are configured such that a pump having an inflow rate of up to about 0.7 L/min connected to the second channel can maintain fluid pressure inside an organ.

44 Claims, 19 Drawing Sheets

(56) References Cited

U.S. PATENT DOCUMENTS

| | | |
|---|---|---|
| 3,297,022 A | 1/1967 | Wallace |
| 3,791,379 A | 2/1974 | Storz |
| 3,850,162 A | 11/1974 | Iglesias |
| 3,945,375 A | 3/1976 | Banko |
| 3,996,921 A | 12/1976 | Neuwirth |
| 4,198,958 A | 4/1980 | Utsugi |
| 4,203,444 A | 5/1980 | Bonnell et al. |
| 4,258,721 A | 3/1981 | Parent et al. |
| 4,261,346 A | 4/1981 | Wettermann |
| 4,294,234 A | 10/1981 | Matsuo |
| 4,369,768 A | 1/1983 | Vukovic |
| 4,392,485 A | 7/1983 | Hiltebrandt |
| 4,414,962 A | 11/1983 | Carson |
| 4,449,538 A | 5/1984 | Corbitt et al. |
| 4,543,965 A | 10/1985 | Pack et al. |
| 4,567,880 A | 2/1986 | Goodman |
| 4,601,290 A | 7/1986 | Effron et al. |
| 4,606,330 A | 8/1986 | Bonnet |
| 4,630,598 A | 12/1986 | Bonnet |
| 4,700,694 A | 10/1987 | Shishido |
| 4,706,656 A | 11/1987 | Kuboto |
| 4,737,142 A | 4/1988 | Heckele |
| 4,756,309 A | 7/1988 | Sachse et al. |
| 4,867,157 A | 9/1989 | McGurk-Burleson et al. |
| 4,924,851 A | 5/1990 | Ognier et al. |
| 4,950,278 A | 8/1990 | Sachse et al. |
| 4,955,882 A | 9/1990 | Hakky |
| 4,998,527 A | 3/1991 | Meyer |
| 4,998,914 A | 3/1991 | Wiest et al. |
| 5,027,792 A | 7/1991 | Meyer |
| 5,037,386 A | 8/1991 | Marcus et al. |
| 5,105,800 A | 4/1992 | Takahashi et al. |
| 5,106,364 A | 4/1992 | Hayafuji et al. |
| 5,125,910 A | 6/1992 | Freitas |
| 5,133,713 A | 7/1992 | Huang et al. |
| 5,152,744 A | 10/1992 | Krause et al. |
| 5,158,553 A | 10/1992 | Berry et al. |
| 5,163,433 A | 11/1992 | Kagawa et al. |
| 5,169,397 A | 12/1992 | Sakashita et al. |
| 5,176,677 A | 1/1993 | Wuchinich |
| 5,195,541 A | 3/1993 | Obenchain |
| 5,244,459 A | 9/1993 | Hill |
| 5,254,117 A | 10/1993 | Rigby et al. |
| 5,269,785 A | 12/1993 | Bonutti |
| 5,275,609 A | 1/1994 | Pingleton et al. |
| 5,288,290 A | 2/1994 | Brody |
| 5,312,399 A | 5/1994 | Hakky et al. |
| 5,312,430 A | 5/1994 | Rosenbluth et al. |
| 5,320,091 A | 6/1994 | Grossi et al. |
| 5,347,992 A | 9/1994 | Pearlman et al. |
| 5,364,395 A | 11/1994 | West |
| 5,374,253 A | 12/1994 | Burns, Sr. et al. |
| 5,392,765 A | 2/1995 | Muller |
| 5,409,013 A | 4/1995 | Clement |
| 5,429,601 A | 7/1995 | Conley et al. |
| 5,449,356 A | 9/1995 | Walbrink et al. |
| 5,456,689 A | 10/1995 | Kresch et al. |
| 5,492,537 A | 2/1996 | Vancaillie |
| 5,498,258 A | 3/1996 | Hakky et al. |
| 5,527,331 A | 6/1996 | Kresch et al. |
| 5,549,541 A | 8/1996 | Muller |
| 5,556,378 A | 9/1996 | Storz et al. |
| 5,569,164 A | 10/1996 | Lurz |
| 5,569,254 A | 10/1996 | Carlson et al. |
| 5,603,332 A | 2/1997 | O'Connor |
| 5,630,798 A | 5/1997 | Beiser et al. |
| 5,674,179 A | 10/1997 | Bonnet et al. |
| 5,695,448 A | 12/1997 | Kimura et al. |
| 5,730,752 A | 3/1998 | Alden et al. |
| 5,741,287 A | 4/1998 | Alden et al. |
| 5,749,885 A | 5/1998 | Sjostrom et al. |
| 5,749,889 A | 5/1998 | Bracich et al. |
| 5,759,185 A | 6/1998 | Grinberg |
| 5,772,634 A | 6/1998 | Atkinson |
| 5,775,333 A | 7/1998 | Burbank et al. |
| 5,807,240 A | 9/1998 | Muller et al. |
| 5,814,009 A | 9/1998 | Wheatman |
| 5,840,060 A | 11/1998 | Beiser et al. |
| 5,913,867 A | 6/1999 | Dion |
| 5,944,668 A | 8/1999 | Vancaillie et al. |
| 5,947,990 A | 9/1999 | Smith |
| 5,956,130 A | 9/1999 | Vancaillie et al. |
| 6,032,673 A | 3/2000 | Savage et al. |
| 6,039,748 A | 3/2000 | Savage et al. |
| 6,068,641 A | 5/2000 | Varsseveld |
| 6,086,542 A | 7/2000 | Glowa et al. |
| 6,090,123 A | 7/2000 | Culp et al. |
| 6,113,594 A | 9/2000 | Savage |
| 6,132,448 A | 10/2000 | Perez et al. |
| 6,149,633 A | 11/2000 | Maaskamp |
| 6,156,049 A | 12/2000 | Lovato et al. |
| 6,159,160 A | 12/2000 | Hsei et al. |
| 6,159,209 A | 12/2000 | Hakky |
| 6,258,111 B1 | 7/2001 | Ross et al. |
| 6,358,200 B1 | 3/2002 | Grossi |
| 6,585,708 B1 | 7/2003 | Maaskamp |
| 6,626,827 B1 | 9/2003 | Felix et al. |
| 6,632,182 B1 | 10/2003 | Treat |
| 6,656,132 B1 | 12/2003 | Ouchi |
| 7,150,713 B2 | 12/2006 | Shener et al. |
| 2002/0058859 A1 | 5/2002 | Brommersma |
| 2003/0050603 A1 | 3/2003 | Todd |
| 2005/0043690 A1 | 2/2005 | Todd |
| 2006/0036132 A1 | 2/2006 | Renner et al. |

FOREIGN PATENT DOCUMENTS

| | | |
|---|---|---|
| DE | 3601453 | 9/1986 |
| DE | 3615694 | 11/1987 |
| DE | 19633124 | 5/1997 |
| EP | 0327410 | 8/1989 |
| EP | 0557044 | 8/1993 |
| GB | 2093353 | 9/1982 |
| GB | 2311468 | 10/1997 |
| JP | 01-75416 | 5/1989 |
| JP | 2002-529185 | 9/2002 |
| JP | 2003-245247 | 9/2003 |
| NL | 1006944 | 5/1999 |
| WO | WO93/07821 | 4/1993 |
| WO | 93/15664 | 8/1993 |
| WO | WO93/15664 | 8/1993 |
| WO | 94/26181 | 11/1994 |
| WO | 95/10982 | 4/1995 |
| WO | WO95/30377 | 11/1995 |
| WO | WO96/11638 | 4/1996 |
| WO | 9911184 | 3/1999 |
| WO | WO00/28890 | 5/2000 |
| WO | WO03/022164 | 3/2003 |

OTHER PUBLICATIONS

"From Distention to Deficit Monitoring Taking the All-In-One Approach", W.O.M. World of Medicine (2 pages).
Karl Storz, "Pilot a Course to Successful Outcome", 2001 InterMetro Industries Corporation (2 pages).
Gynecare, "Fluid Management System" Instruction for Use (26 pages).
C.R. Bard, Inc , "The HydoFlex HD System" (1 page).
"HysteRo-Purator 1143-1 Technical Data" (2 pages).
Richard Wolf "The Fluid Manager" (2 pages).
ACMI Corporation, "Dolphin II and Destin-U-Flo Fluid Management Systems for Hysteroscopy", ACMI Corporation, 2002 (1 page).
ACMI Corporation, "Dolphin II Hysteroscopic Fluid Management Systems", ACMI Corporation, 2002 (1 page).
Richard Wolf, "Morce—Power 2306" Electronic Morcellator (2 pages).
Gynecare X-Tract, "Tissue Morcellator", Instruction for Use (3 pages).
Gynecare "Motor Drive Unit", Instructions for Use4 (3 pages).
Notice of Reasons for Rejection for Japanese Application No. 2007-530014, mailed Feb. 7, 2012, 2 pages.
Defendant Hologic Inc.'s Preliminary, Non-Binding List of Asserted Prior Art References in *Smith & Nephew, Inc. v. Hologic, Inc.*, Civil

(56) References Cited

OTHER PUBLICATIONS

Action Nos. 11-CV-12064-RWZ and 10-CV-10951-RWZ, U.S. District Court for the District of Massachusetts, Feb. 8, 2012, 8 pages.
Baggish et al., "Instrumentation for Hysteroscopy," in "Diagnostic and Operative Hysterectomy," Mosby (1999).
Baggish et al., "Accessory Instruments for Operative Hysteroscopy," in "Diagnostic and Operative Hysterectomy," Mosby (1999).
Neis et al., "Hysteroscopy: Textbook and Atlas," 91-103, Thieme Medical Publishers (1994).
Sugimoto et al., "A Color Atlas of Hysteroscopy," 6-7, Springer (1999).
Weck, a Squibb Company: Direct Path to Diagnostic and Operative Control, Advertisement, Journal of Gynecologic Surgery, vol. 7 (1991).
International Search Report for International Application No. PCT/US2005/029807, mailed Jun. 13, 2006, 6 pages.
Hologic's Opposition to Smith & Nephew's Motion for Preliminary Injunction, Redacted, *Smith & Nephew, Inc.* v. *Hologic, Inc.*, Civil Action No. 11-CV-12064-RWZ, filed Dec. 30, 2011, 26 pages.
Exhibit P To Hologic's Opposition to Smith & Nephew's Motion for Preliminary Injunction, Redacted, *Smith& Nephew, Inc.* v. *Hologic, Inc.*, Civil Action No. 11-CV-12064-RWZ, filed Dec. 30, 2011, 99 pages.
European Patent Office Examination Report for Application No. 05 786 521.4-2305 dated Apr. 21, 2010, 4 pages.
European Patent Office Examination Report for Application No. 05 786 521.4-2305 dated Sep. 26, 2010, 5 pages.
PCT International Preliminary Report on Patentability for Application No. PCT/US2005/029807 dated Feb. 28, 2007, 9 pages.
Gregory Bacsko, Uterine Surgery by Operative Hysteroscopy, 71 European Journal of Obstetrics Gynecology and Reproductive Biology, 219-222 (1997).
Emanuel et al., Long-term Results of Hysteroscopic Myomectomy for Abnormal Uterine Bleeding, 93:5 Obstet Gynecoogy, 743-748 (1999).
Gerber S, et al., The Endoscapel: A New Endoscopic Instrument for Supracervical Hysterectomy and Morcellation of Masses: Clinical Evaluation, 86: Suppl. 1, European Journal of Obstetrics & Gynecology and Reproductive Biology, S12 (1999).
Karl Storz, Advertisement, Journal of Gynecologic Surgery, vol. 5 (1989).
Karl Storz Uterine Resectoscopes for Endometrial Ablation and Resection, Advertisement, Journal of Gynecologic Surgery, vol. 6 (1990).
Lin et al., Clinical Applications of a New Fujinon Operating Fiberoptic Hysteroscope, 6 Journal of Gynecologic Surgery, 81-87 (1990).
Mettler et al., Pelviscopic Uterine Surgery 6 Surgical Endoscopy, 23-31 (1992).

TISSUE RESECTING SYSTEM

CROSS-REFERENCE TO RELATED APPLICATIONS

The present application is a continuation of U.S. patent application Ser. No. 13/212,240, filed Aug. 18, 2011, titled TISSUE RESECTING SYSTEM, now allowed, which is a continuation U.S. patent application Ser. No. 10/927,244, filed Aug. 27, 2004, titled TISSUE RESECTING SYSTEM, now U.S. Pat. No. 8,062,214. The contents of the prior applications are incorporated herein by reference in their entirety.

TECHNICAL FIELD

This invention relates to a tissue resecting system.

BACKGROUND

Endoscopic surgery of a distensible organ, such as a uterus, may be performed with an endoscope that is insertable into the uterus and a resector that passes through the endoscope to cut or otherwise treat tissue in the uterus. During surgery, it often is desirable to distend the uterus with a fluid, such as saline, sorbitol, or glycine, in order provide a visible working space. Fluid can be infused into the uterus and removed from the uterus through the endoscope and/or resector.

SUMMARY

If the outflow of fluid from the uterus is greater than the inflow of fluid to the uterus, the uterus may collapse back to its normal state, making visualization of the uterus difficult. On the other hand, if the inflow of fluid is greater than the outflow of fluid such that the pressure created by the fluid is greater than the patient's mean arterial pressure, excess fluid can enter the patient's vascular system (known as intravasation), which can lead to serious complications or death.

To aid in addressing these issues, in an aspect of the invention, a surgical system includes a first instrument defining a fluid flow channel and a second instrument receivable by the first instrument fluid flow channel. The second instrument defines a channel. The system includes a valve coupled to the first instrument and configured to control fluid flow through the first instrument channel. The valve is configured such that impedance of fluid flow through the first instrument channel is substantially the same without the second instrument received in the first instrument channel and with the first instrument channel partially blocked by the second instrument such that the first instrument channel is limited to a region between the first and second instruments.

Embodiments of this aspect of the invention may include one or more of the following features.

For example, the first instrument includes an outer member and an inner member. The inner member defines the first instrument channel therethrough. The inner member is received within the outer member, and the outer member and the inner member define a second fluid flow channel therebetween. The second instrument includes a tube defining the second instrument channel therethrough. The tube partially blocks the first instrument fluid flow channel when received therein. The second fluid flow channel has a cross-sectional area of, e.g., about 0.0083 to about 0.0249 square inches, preferably about 0.0166 square inches. The first instrument fluid flow channel has a cross-sectional area of, e.g., about 0.0053 to about 0.0159 square inches, preferably about 0.0106 square inches. The second instrument channel has a cross-sectional area of, e.g., about 0.0042 to about 0.013 square inches, preferably about 0.0085 square inches.

In an illustrated embodiment, the valve includes a housing and a body within the housing. The body defines an opening therein and is moveable relative to the housing between a first position in which the opening and the first instrument channel define a first fluid flow path having a first impedance and a second position in which the opening is arranged to receive the second instrument therethrough such that the opening and the first instrument channel define a second fluid flow path that has a second impedance substantially equal to the first impedance.

The system as illustrated includes a pump and the first instrument is configured to connect to the pump such that the pump infuses fluid through the first instrument channel. The pump is programmed to infuse fluid through the first instrument channel to maintain a substantially constant pressure of between about 60 mm Hg and about 120 mm Hg inside a distensible organ. A sensor coupled to the pump senses a flow impedance at a given flow rate, and a controller coupled to the sensor and the pump compares the flow impedance to a predetermined flow impedance for the given flow rate to verify the identity of the first and second instruments.

The second instrument channel is in fluid communication with a source of suction and a regulator is interposed between the second instrument channel and the source of suction to regulate an amount of suction applied through the second instrument channel.

According to another aspect of the invention, a surgical system includes a first instrument defining a fluid flow channel, and a second instrument receivable by the first instrument fluid flow channel. The second instrument defines a channel. The system includes a means for maintaining a substantially constant impedance of fluid flow through the first instrument channel with and without the second instrument received in the first instrument channel.

According to another aspect of the invention, a method includes: (a) positioning a valve coupled to a first instrument in a first position; (b) introducing fluid to a distensible organ through the valve with the valve in the first position and through a channel in the first instrument; (c) positioning the valve in a second position; (d) introducing a second instrument through the valve with the valve in the second position and through the first instrument channel; and (e) introducing fluid to the distensible organ through the valve with the valve in the second position and through a region of the first instrument channel located between the first and second instruments. The impedance of fluid flow in steps (b) and (e) is substantially the same.

Embodiments of this aspect may include one or more of the following features. The method includes maintaining substantially constant fluid pressure within the distensible organ with and without the second instrument received in the first instrument channel. Maintaining includes suctioning fluid from the distensible organ through the second instrument. The method includes regulating a pump coupled to the valve for introducing fluid through the valve.

According to another aspect of the invention, a valve includes a housing and a body within the housing. The body defines an opening therein. The body is moveable relative to the housing between a first position in which the opening and the housing define a first fluid flow path having a first impedance and a second position in which the opening is arranged to receive a surgical instrument therein. The opening is configured such that with the surgical instrument received therein, the opening and the housing define a second fluid flow path that has a second impedance substantially equal to the first impedance.

Embodiments of this aspect may include one or more of the following features. The opening includes a throughbore through the body for receiving the surgical instrument. The opening includes a second bore having a first open end and a second closed end in the body. The second bore is arranged substantially orthogonal to the throughbore and intersects the throughbore. The housing defines an inlet and an outlet. When the body is in the first position, the throughbore is partially aligned with the inlet and the first fluid flow path is from the inlet, through the throughbore, and then through the second bore to the outlet. When the body is in the second position, the second bore is aligned with the inlet and the second fluid flow path is from the inlet, through the second bore, and then through the throughbore to the outlet.

According to another aspect of the invention, a method of regulating inflow through a valve includes positioning the valve in a first position wherein the valve has a first impedance; positioning the valve in a second position; and introducing a surgical instrument through the valve in the second position. A combination of the surgical instrument and the valve has a second impedance substantially equal to the first impedance.

According to another aspect of the invention, an apparatus for surgery includes an outer member and an inner member received within the outer member. The outer member and the inner member define a first channel therebetween. The inner member houses an optical lens and defines a second channel for receiving a surgical instrument. The first and second channels are configured such that a pump having an inflow rate of up to about 0.7 L/min connected to the second channel can maintain fluid pressure inside an organ.

Embodiments of this aspect may include one or more of the following features. A pump is coupled to the second channel to introduce fluid through the second channel at an inflow rate up to about 0.7 L/min. The outer member defines a plurality of holes in fluid communication with the first channel. The plurality of holes is positioned in a distal portion of the outer member. The second channel has a D-shaped cross-section. The first channel has a cross-sectional area, e.g., of about 0.0083 to about 0.0249 square inches, preferably about 0.0166 square inches. The second channel has a cross-sectional area of, e.g., about 0.0053 to about 0.0159 square inches, preferably about 0.0106 square inches. The second channel receives the surgical instrument. The surgical instrument has a suction channel with a cross-sectional area of, e.g., about 0.0042 to about 0.013 square inches, preferably about 0.0085 square inches. A valve is coupled to the inner member for regulating inflow through the second channel such that the valve and the second channel have a first impedance equal to a second impedance when the surgical instrument is received in the second channel.

According to another aspect of the invention, a fluid management system includes a pump configured for coupling to an endoscope to infuse fluid through the endoscope at a given flow rate. A sensor is coupled to the pump that senses a flow impedance through the endoscope at the given flow rate. A controller is coupled to the sensor and programmed to compare the flow impedance to a predetermined flow impedance for the given flow rate to verify the identity of the endoscope and a surgical instrument received therein.

Embodiments of this aspect may include one or more of the following features. The sensor includes a pressure transducer. A circuit is coupled to the controller and the pump for disabling the pump if the identity of the surgical instrument and endoscope is not verified. The controller is programmed to compare flow impedances to predetermined flow impedances at multiple flow rates.

According to another aspect of the invention, a fluid management system includes means for infusing fluid through an endoscope at a flow rate, means for measuring a flow impedance through the endoscope at the flow rate, and means for comparing the flow impedance to a predetermined flow impedance to verify the identity of the endoscope and a surgical instrument received therein.

According to another aspect of the invention, a method includes programming a pump with data on a predetermined flow impedance for an endoscope and surgical instrument assembly for a given flow rate, activating the pump to infuse fluid through the endoscope and surgical instrument assembly at the given flow rate, sensing a flow impedance through the assembly, and comparing the sensed flow impedance to the predetermined flow impedance. The method may further include disabling the pump if the flow impedance is not within a threshold value of the predetermined flow impedance.

According to another aspect of the invention, a method includes infusing fluid into a distensible organ, and maintaining a substantially constant fluid pressure inside the distensible organ between about 60 mm Hg and about 120 mm Hg.

According to another aspect of the invention, a system includes an endoscope defining a channel therethrough and a surgical instrument received within the endoscope channel. The surgical instrument defines a channel therein for connection with a source of suction. A regulator is coupled to the surgical instrument channel between the instrument channel and the source of suction to regulate an amount of suction applied through the instrument channel.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
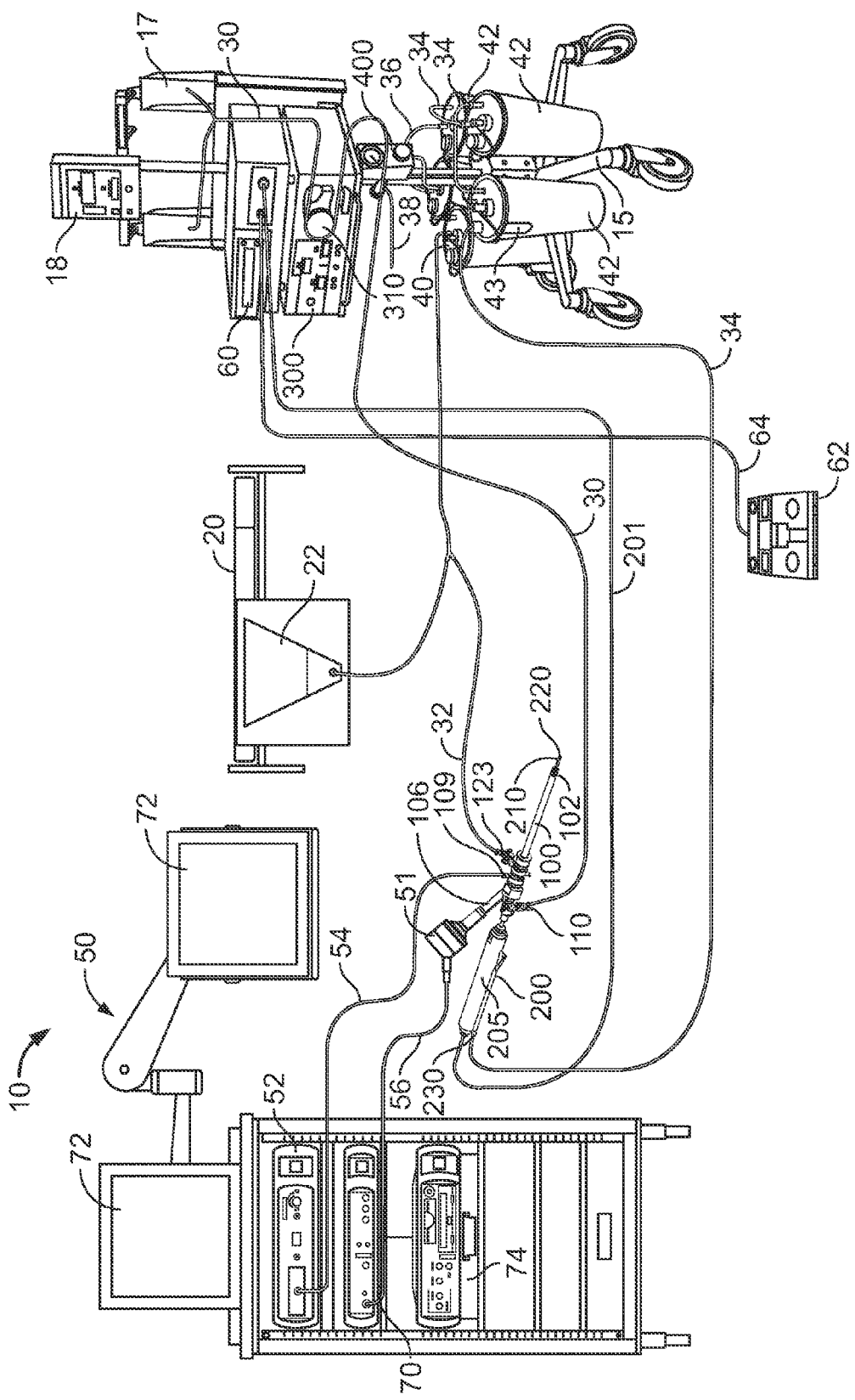
FIG. 1 is a schematic diagram of a resection system.

Referring to FIG. 1, a tissue resecting system 10 includes an endoscope, e.g., hysteroscope 100, having a distal portion 102 insertable into a distensible organ, e.g., a uterus, of a patient 20 to flow fluid into and remove fluid from the organ. System 10 includes a cart carrying fluid bags 17 that are connected to hysteroscope 100 by an inflow line 30 to deliver fluid to hysteroscope 100. Inflow line 30 runs through a pump, e.g., peristaltic pump 310, of a fluid management control unit 300 on cart 15. Pump 310 controls the pressure of the fluid delivered along inflow line 30 to hysteroscope 100. System 10 also includes a gravity container 40 on cart 15 connected by an outflow line 32 to an outflow valve 105 on hysteroscope 100 to collect the outflow of fluid from hysteroscope 100, under the force of gravity. In addition, system 10 includes a surgical drape 22 connected by outflow line 32 to gravity container 40 to collect fluid from patient 20.

System 10 further includes a resector 200 that is received within hysteroscope 100 during use to resect tissue from the organ. Resector 200 includes a handle 205 and a distal portion 210 that extends out of distal portion 102 of hysteroscope 100. Distal portion 210 includes a working end 220, e.g., a morcellator, that can be actuated to cut tissue from the organ. Handle 205 includes a motor (not shown) coupled to working end 220 to rotate working end 220 about a longitudinal axis to cut tissue. Also located on cart 15 is a resector control unit 60 of system 10 connected by a wire 201 to resector 200 to control movement of working end 220. System 10 also includes a footpedal 62 connected to control unit 60 by a wire 64 to actuate control unit 60.

Also located on cart 15 are four vacuum containers 42 of system 10 connected by suction line 34 to a suction port 230 on resector 200 to collect fluid and tissue suctioned through resector 200. At least one of vacuum containers 42 includes a tissue trap 43 that collects tissue suctioned through suction lines 34 for later examination, e.g., by a pathologist. System 10 also includes a vacuum regulator 400 connected by a suction line 36 to vacuum containers 42 and by vacuum line 38 to a vacuum source (not shown) to regulate suction provided by the vacuum source through suction channel 204 of resector 200.

Also located on cart 15 is a fluid monitoring unit 18 of system 10 that tracks the amount of fluid collected in gravity container 40 and vacuum containers 42 and the amount of fluid pumped by fluid management control unit 300 and sets off an audible or visual alarm if the difference between the amounts of fluid pumped and collected is above a threshold value, thus minimizing the possibility of excess fluid intravasation.

Part of system 10 is a visualizing and imaging assembly 50 that includes a camera 51 coupled to a camera port 106 of hysteroscope 100, and a light source 52 coupled by a fiber optic cable 54 to a light port 109 of hysteroscope 100. Together, camera 50 and light source 52 allow a user to remotely visualize the tissue at distal end 102 of hysteroscope 100. Assembly 50 also includes an imaging station 70 connected by a fiber optic cable 56 to camera 50. Imaging station 70 has monitors 72 for viewing images from camera 50 and a capture system 74 for making a recording of the images.

Figure 2A:
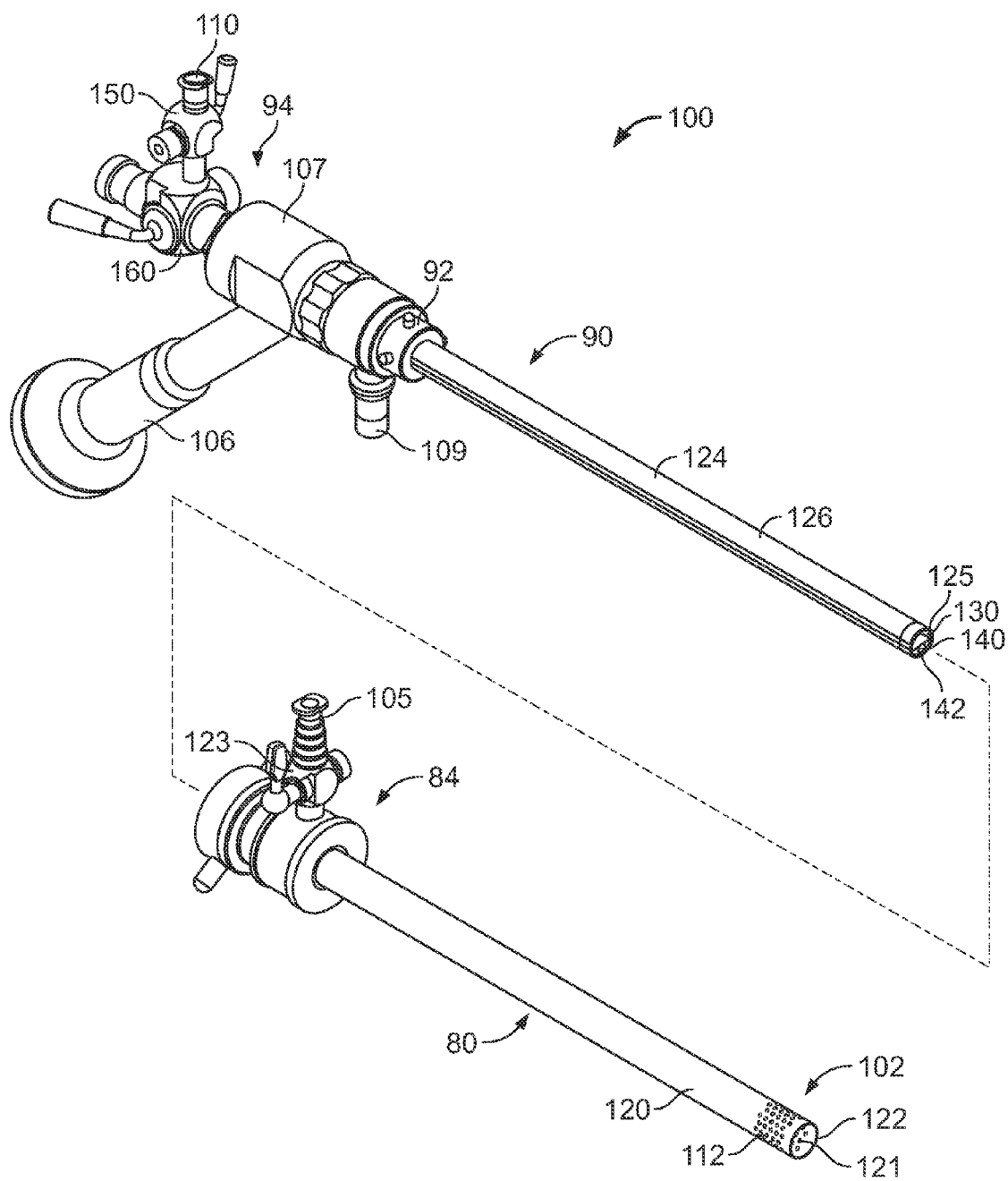
FIG. 2A is an exploded, perspective view of a hysteroscope of the system of FIG. 1.
Figure 2B:
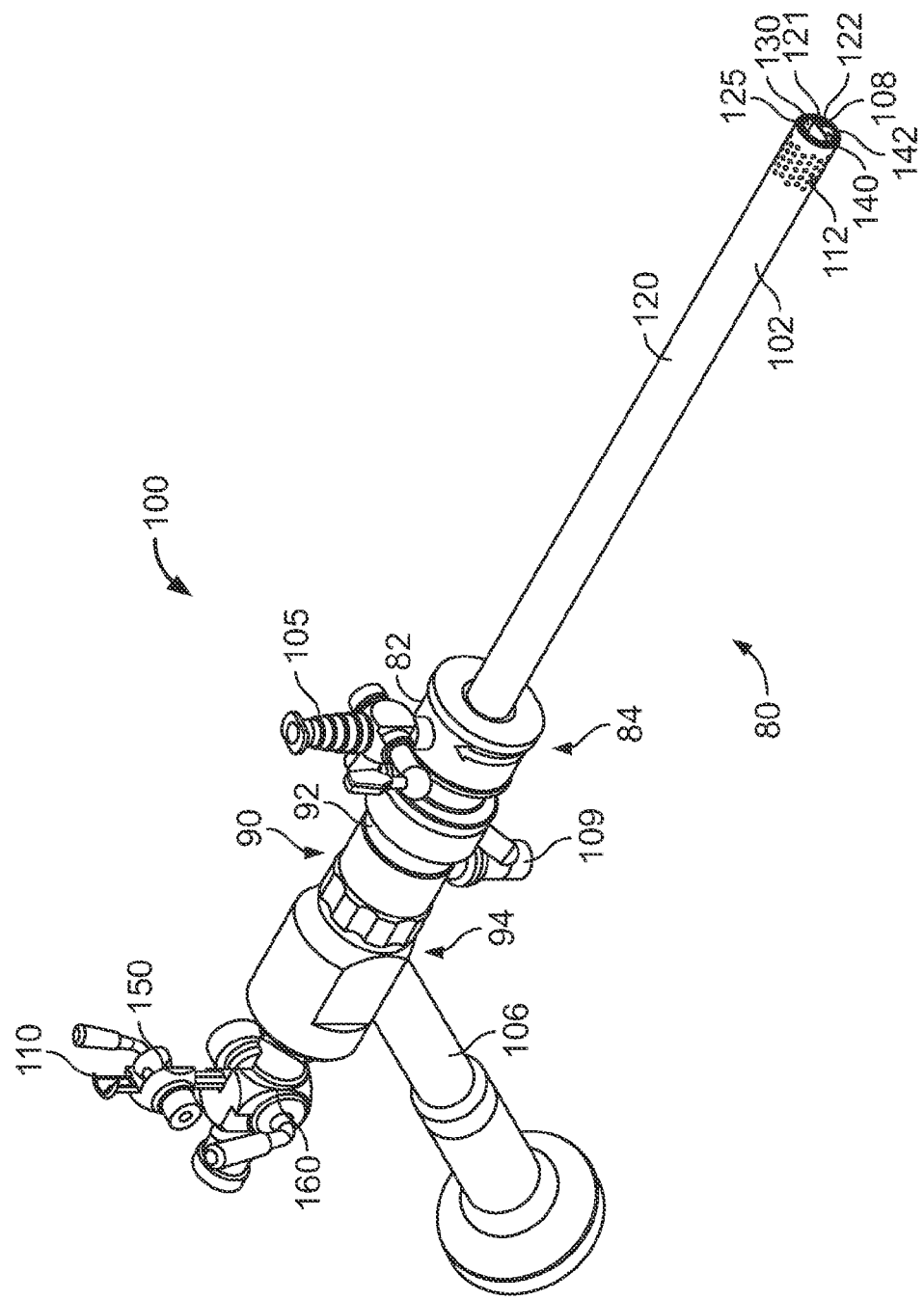
FIG. 2B is a perspective view of the assembled hysteroscope of FIG. 2A.

Referring to FIGS. 2A and 2B, hysteroscope 100 includes a sheath 80 that has a tube 120 with an inner wall 122 defining a channel 121 therethrough. Distal end 102 of tube 120 includes a plurality of holes 112 in communication with channel 121 for allowing fluid to flow out of an organ through channel 121. Sheath 80 has a proximal portion 84 that includes outflow port 105. Outflow port 105 is in fluid communication with channel 121. Positioned between outflow port 105 and channel 121 is an on/off valve 123 for turning on and off fluid flow from channel 121 to outflow port 105.

Hysteroscope 100 also includes a scope housing 90 that has an elongated member 124 removably receivable in tube 120. Member 124 has an outer wall 126 and an inner wall 125. Inner wall 125 that defines an inflow channel 130. A proximal portion 94 of scope housing 90 includes inflow port 110, a primary valve 150, and a secondary valve 160, which are fluidly connected to inflow channel 130, as described below. Member 124 also defines a lens channel 140 that houses an optical lens 142. Scope housing 90 has a proximal portion 94 that includes camera port 106 and light port 109, which are coupled to optical lens 142 by fiber optic lines (not shown). Light travels from light port 109 to distal end 102 of hysteroscope 100 to illuminate objects near distal end 102. Images of those objects are received by optical lens 142, and travel through camera port 106 to camera (FIG. 1), to allow the user to view the organ through hysteroscope 100. Lens channel 140 is positioned adjacent to inflow channel 130 to help keep optical lens 142 clear of debris during use. Proximal portion 94 of scope housing 90 also includes a pin 92 receivable in a J-shaped slot (not shown) in sheath 80 to releasably lock scope housing 90 to sheath 80 when member 124 is received in tube 120.

Figure 3A:
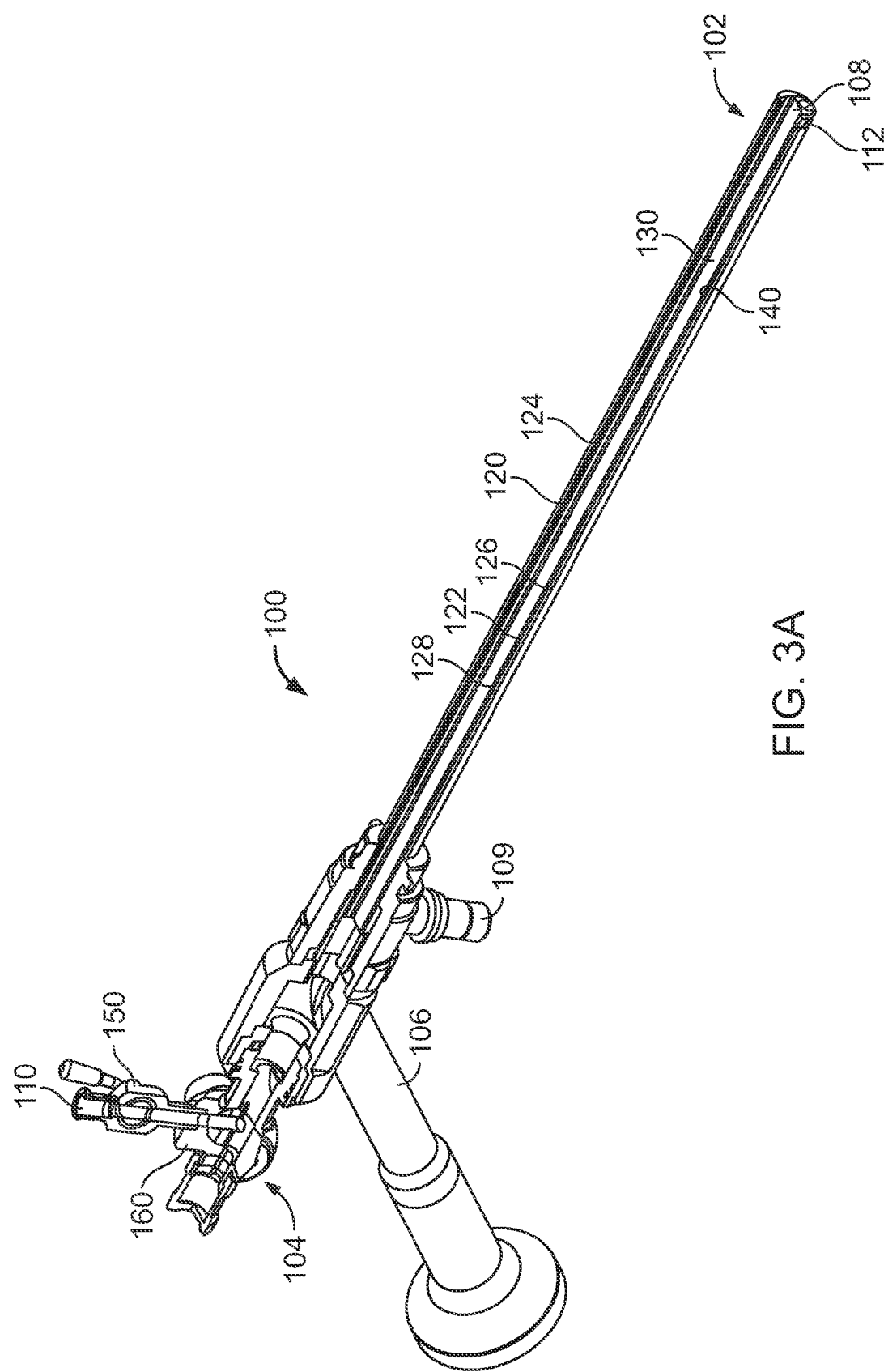
FIG. 3A is a longitudinal cross-sectional view of the hysteroscope of FIG. 2B.
Figure 3B:
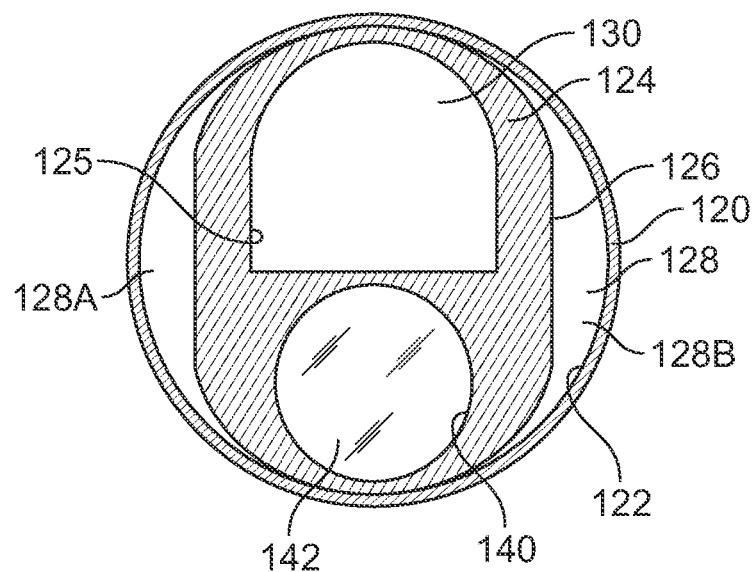
FIG. 3B is a cross-sectional view of the hysteroscope of FIG. 2B taken along line 3B-3B.

Referring also to FIGS. 3A and 3B, when member 124 is received in tube 120, inner wall 122 of tube 120 and outer wall 126 of member 124 define a passive outflow channel 128 therebetween. Passive outflow channel 128 is divided into a left portion 128A and a right portion 128B, which reconnect at outflow port 105. Passive outflow channel 128 is in fluid communication with holes 112 in distal end 102 of tube 120 and with outflow port 105 to permit passive outflow of fluid from the organ under the force of gravity. It will be understood that outflow channel 128 need not be divided. Inner wall 125 of member 124 defines inflow channel 130 that is in fluid communication with an aperture 108 in distal end 102 of hysteroscope 100 to permit fluid flow into the organ. Fluid flows through passive outflow channel 128 along a path that is completely separate from a path along which fluid flows through inflow channel 130.

Referring to FIG. 3B, inflow channel 130 and passive outflow channel 128 are sized and configured so that fluid management control unit 300, which has an inflow rate of up to 0.7 L/min, is able to maintain a substantially constant fluid pressure inside a distensible organ by pumping sufficient fluid into the organ through inflow channel 130 to balance fluid flow out of the organ through passive outflow channel 128, as described below. For example, inflow channel 130 has a D-shaped cross-section with a cross-sectional area, e.g., of about 0.0153 to about 0.0461 square inches, preferably about 0.0307 square inches, and each portion 128A, 128B of passive outflow channel 128 has a crescent-shaped cross-section with a combined cross-sectional area, e.g., of about 0.0083 to about 0.0249 square inches, preferably about 0.0166 square inches. It should be understood that other configurations and sizes of inflow channel 130 and passive outflow channel 128 are possible, so long as outflow of fluid through outflow channel 128 does not exceed the ability of fluid management control unit 300 to pump fluid into the organ through inflow channel 130 at least at the same flow rate as the outflow of fluid.

Figure 4:
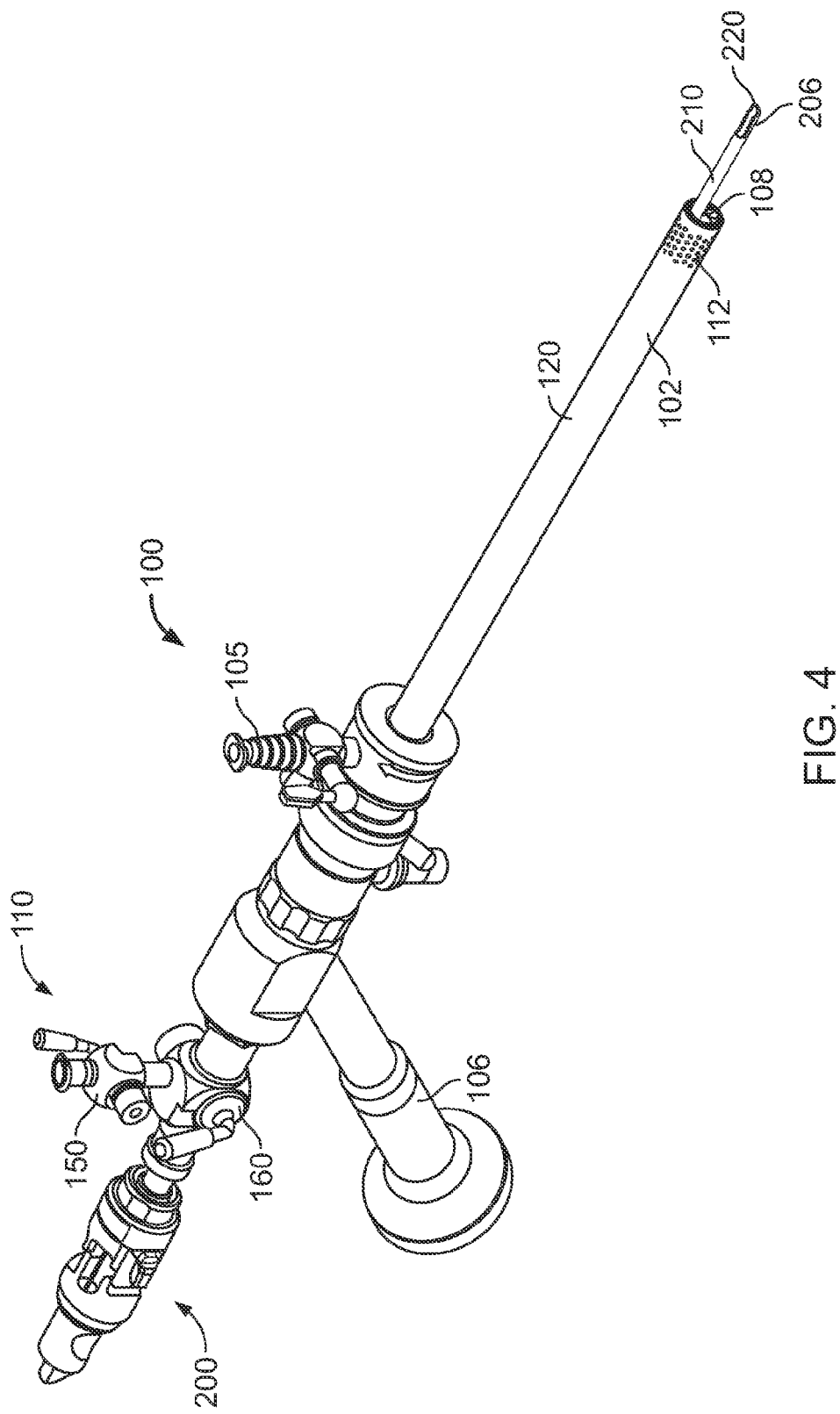
FIG. 4 is a perspective view of the hysteroscope of FIG. 2B with a resector received therethrough.
Figure 5:
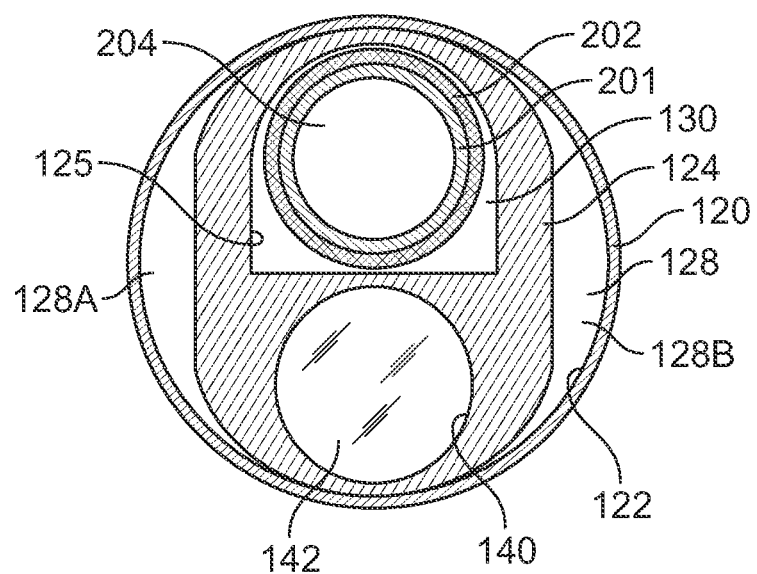
FIG. 5 is a cross-sectional view of the hysteroscope and resector of FIG. 4 taken along line 5-5.

Referring to FIGS. 4 and 5, resector 200 includes a stationary elongated outer tube 202 and a rotatable inner tube 201 that is coupled to working end 220 (not shown). Inflow channel 130 receives resector 200 therethrough. The cross-section of inflow channel 130 enables inflow channel 130 to be only partially blocked by resector 200, allowing fluid to continue to flow into the organ through a region of inflow channel 130 unblocked by resector 200, located between inner wall 125 and elongated tube 202 Inner tube 201 of resector 200 defines a suction channel 204 having an opening 206 at working end 220 of resector 200 and in fluid communication with suction port 230 of resector handle 205 (FIG. 1) to permit suction of fluid and tissue from the organ. Fluid is suctioned through suction channel 204 along a path that is completely separate from the paths along which fluid flows through outflow channel 128 and inflow channel 130.

Referring to FIG. 5, passive outflow channel 128, inflow channel 130, and suction channel 204 are sized and configured so that fluid management control unit 300 is able to maintain the substantially constant fluid pressure inside the organ by pumping sufficient fluid into the organ to balance fluid flow out of the organ through passive outflow channel 128 and suction of fluid out of the organ through suction channel 204, as described below. For example, the portion of inflow channel 130 not blocked by resector 200 has a cross-sectional area of about 0.0106 square inches, passive outflow channel 128 has a cross-sectional area of about 0.0166 square inches, and suction channel 204 has a cross-sectional area of about 0.0085 square inches. It should be understood that other configurations and sizes of inflow channel 130, passive outflow channel 128, and suction channel 204 are possible, so long as outflow of fluid through outflow channel 128 and suction of fluid through suction channel 204 do not exceed the ability of fluid management control unit 300 to pump fluid into the organ through inflow channel 130 at the same flow rate as the outflow of fluid.

Figure 14:
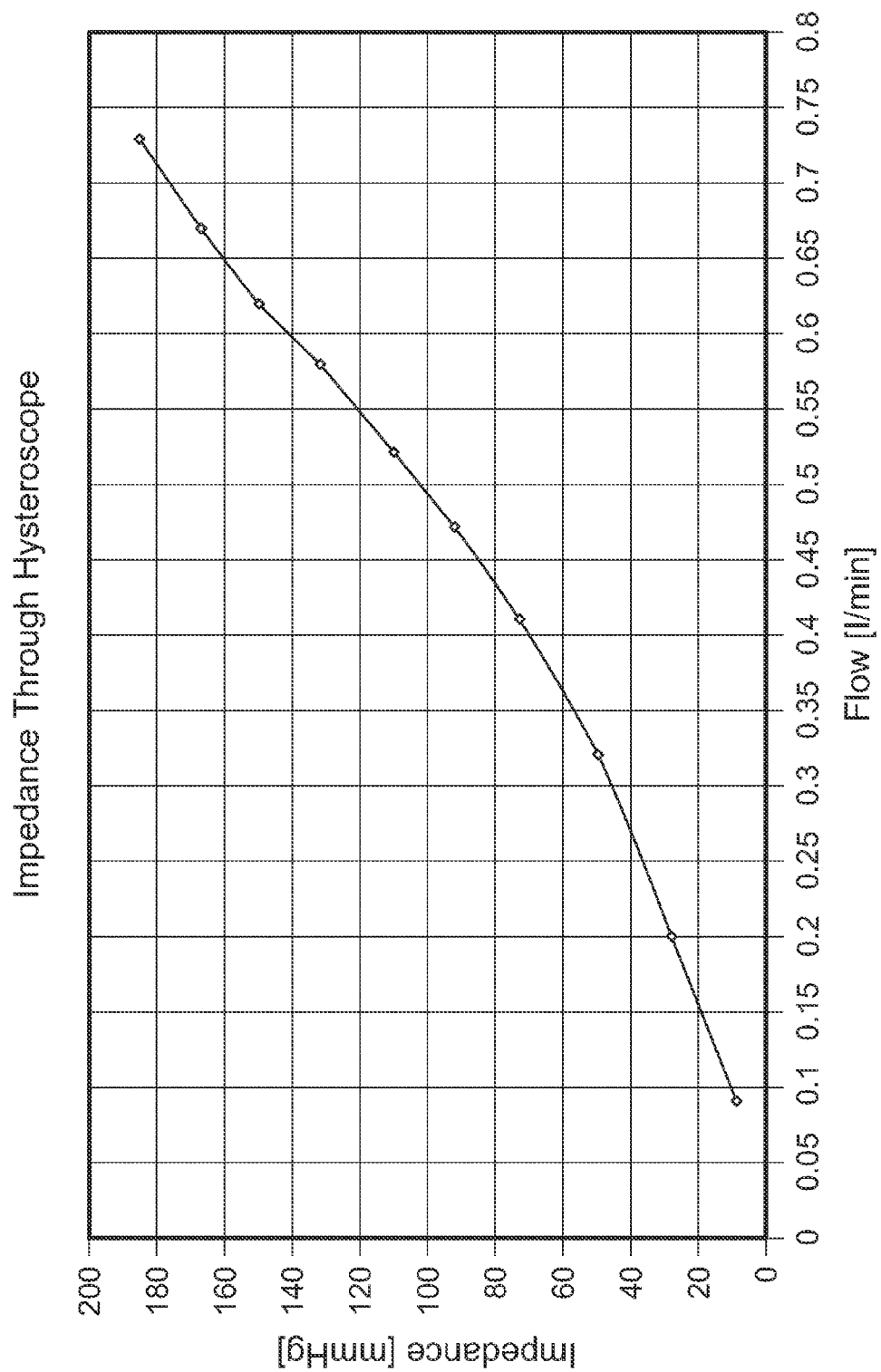
FIG. 14 is a graph showing the impedance through the hysteroscope at various flow rates.

The ability of fluid management control unit 300 to maintain a substantially constant fluid pressure in the organ is further facilitated by secondary valve 160 of scope housing 90, which maintains substantially the same fluid flow impedance through inflow channel 130 regardless of whether resector 200 is positioned in scope housing 90. For example, FIG. 14 shows the impedance through hysteroscope 100 at various flow rates, regardless of whether resector 200 is positioned in scope housing 90. By maintaining a substantially constant fluid flow impedance, secondary valve 160 facilitates fluid management control unit maintaining a substantially constant pressure in the organ regardless of whether resector 200 is positioned in scope housing 90. Impedance refers to the pressure drop in fluid between two points (in this case between inflow port 110 and the distal end of inflow channel 130) and varies proportional to the square of the flow rate.

Figure 6A:
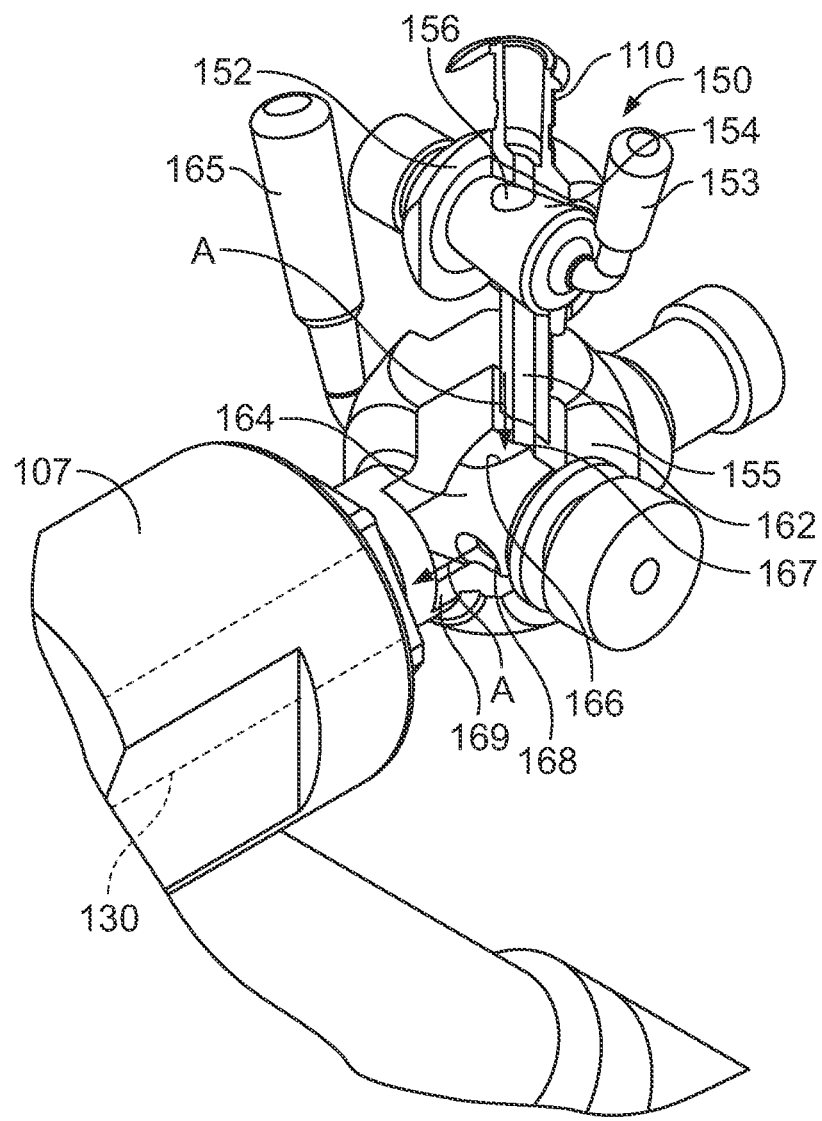
FIG. 6A is a perspective cut-away view of primary and secondary valves of the hysteroscope of FIG. 2B, with the primary valve in an open position and the secondary valve in a first position.
Figure 6B:
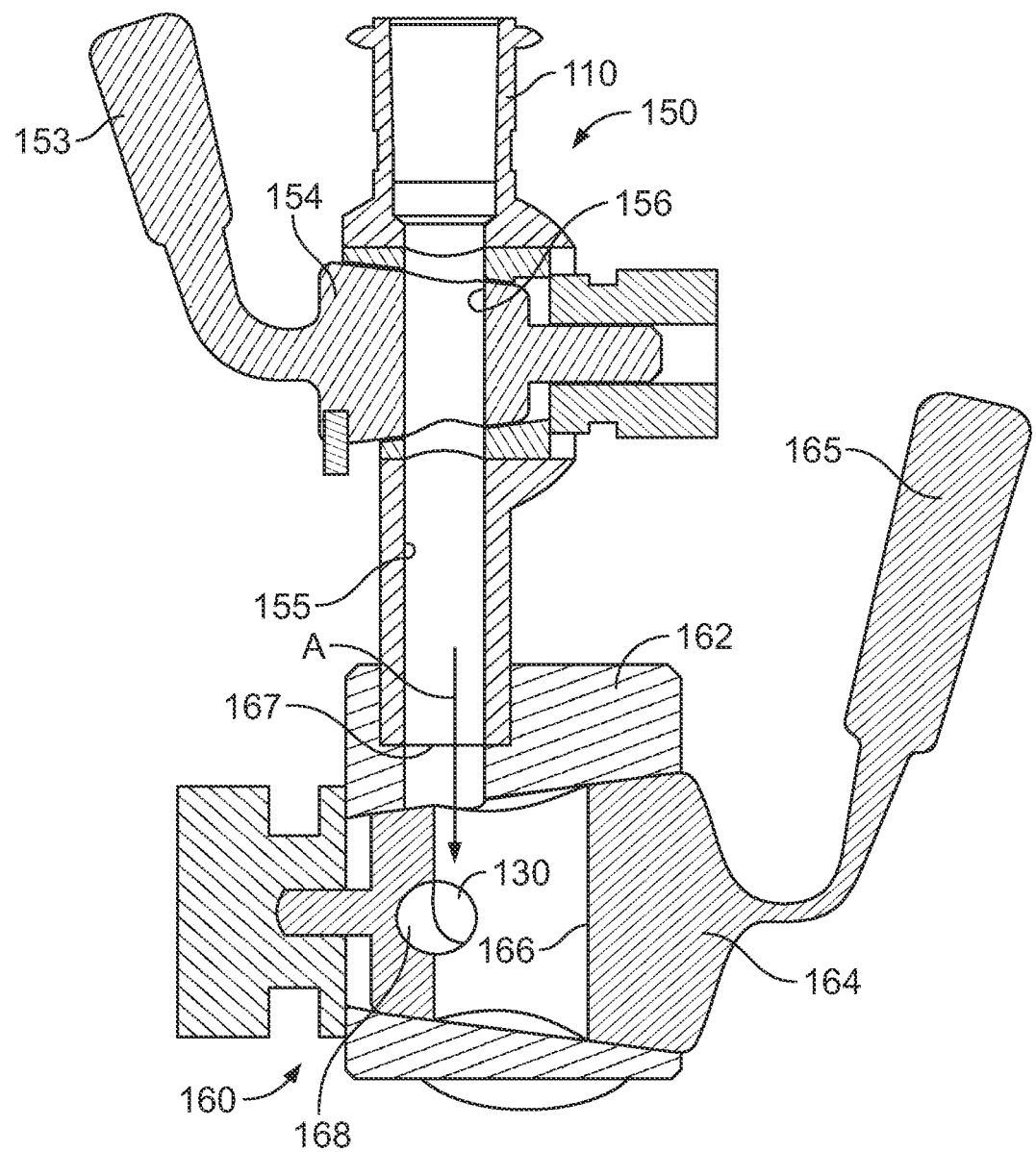
FIG. 6B is a cross-sectional view of the primary and secondary valves as shown in FIG. 6A taken along line 6B-6B.

Referring to FIGS. 6A and 6B, secondary valve 160 has a housing 162 and a body 164 rotatable within housing 162. Housing 162 includes an inlet 167 aligned with inflow port 110 and an outlet 169 aligned with inflow channel 130. Body 164 defines a throughbore 166 and a smaller diameter blind bore 168 having an open end 168A and a closed end 168B. Blind bore 168 intersects throughbore 166 substantially orthogonal to throughbore 166 and has a diameter substantially equal to the diameter of intermediate channel 155.

Body 164 is attached to a handle 165 that allows body 164 to be moveable between a first position (FIGS. 6A-6B) defining a first fluid flow path A and a second position (FIGS. 7A-7B) defining a second fluid flow path B. When secondary valve 160 is in the first position, blind bore 168 is aligned with outlet 169 and throughbore 166 is parallel to, but offset from, inlet 167 such that body 164 partially blocks inlet 167. Fluid flow along path A is impeded by body 164 partially blocking inlet 167.

Figure 7A:
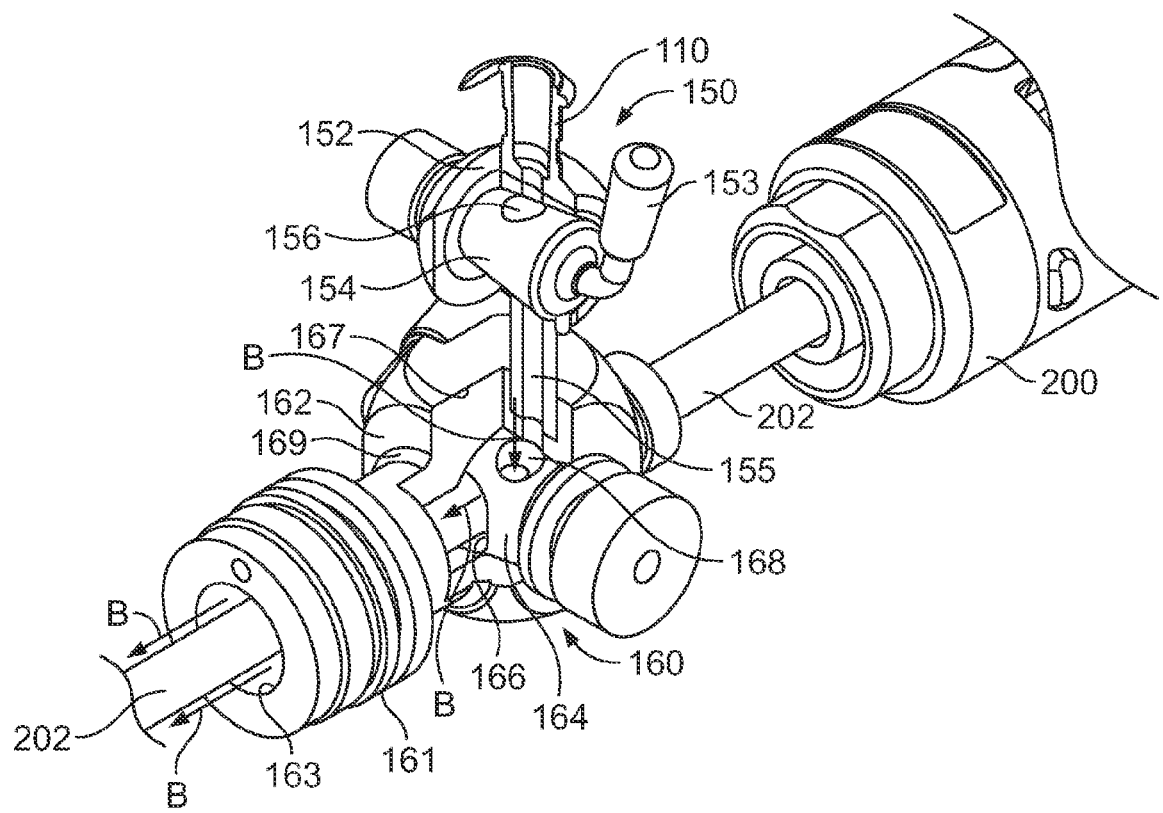
FIG. 7A is a perspective cut-away view of the primary and secondary valves of the hysteroscope of FIG. 2B, with the primary valve in an open position and the secondary valve in a second position for receiving the resector.
Figure 7B:
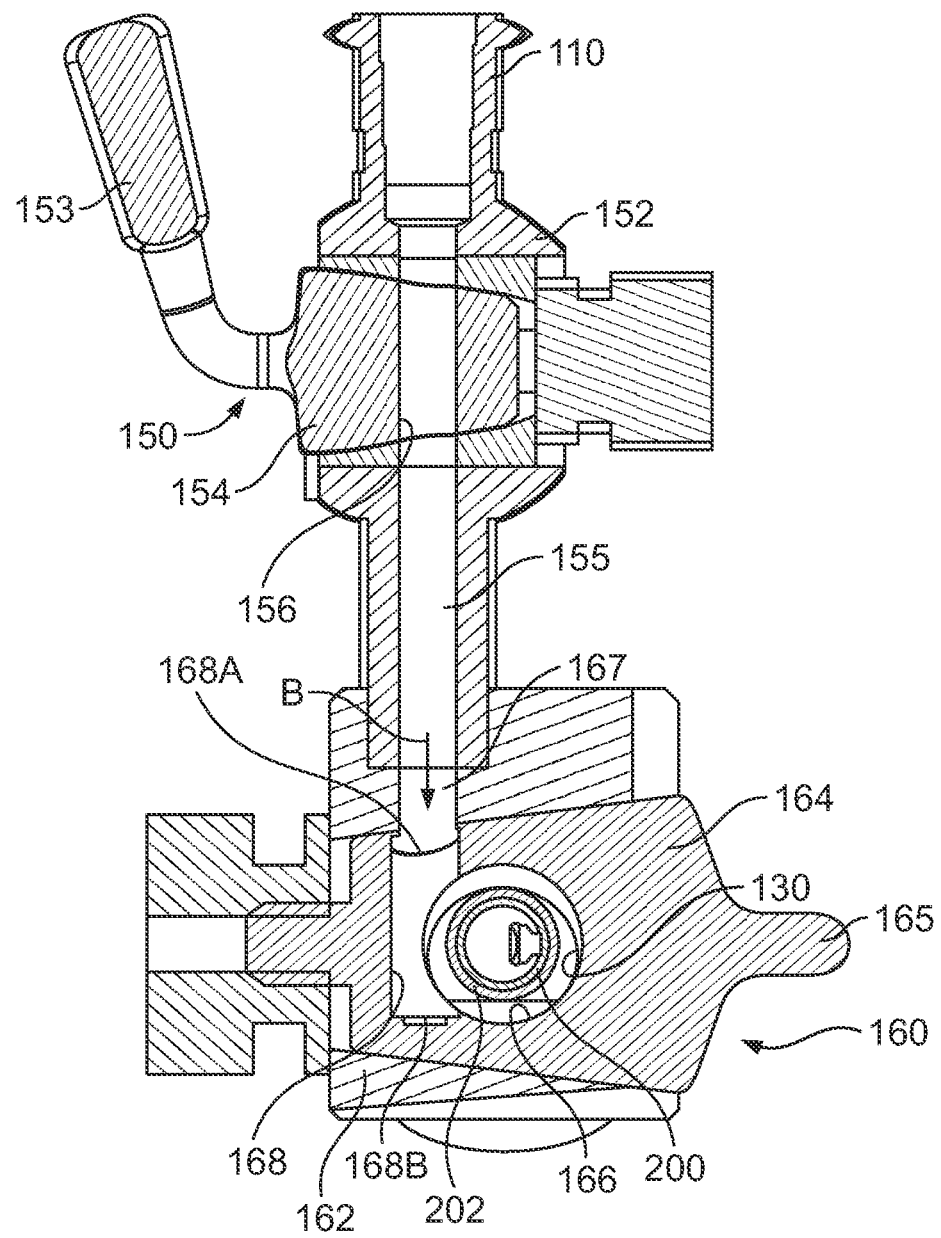
FIG. 7B is a cross-sectional view of the primary and secondary valves as shown in FIG. 7A taken along line 7B-7B.

Referring to FIGS. 7A and 7B, when secondary valve 160 is in the second position, blind bore 168 is aligned with inlet 167 and throughbore 166 is aligned with outlet 169 such that fluid can flow through secondary valve 160 along path B. In use, with secondary valve 160 in the second position, resector 200 is received through throughbore 166 of secondary valve 160, such that resector 200 is received within inflow channel 130 of hysteroscope 130. Fluid flow along path B is impeded by resector 200 partially blocking throughbore 166 and inflow channel 130. The impedance of fluid flow along path B due to resector 200 blocking fluid flow is substantially equal to the impedance of fluid flow along path A due to body 164 blocking fluid flow. Thus, secondary valve 160 allows for substantially the same impedance of fluid flow through inflow channel 130 and into the organ regardless of whether resector 200 is received through hysteroscope 100.

Figure 8A:
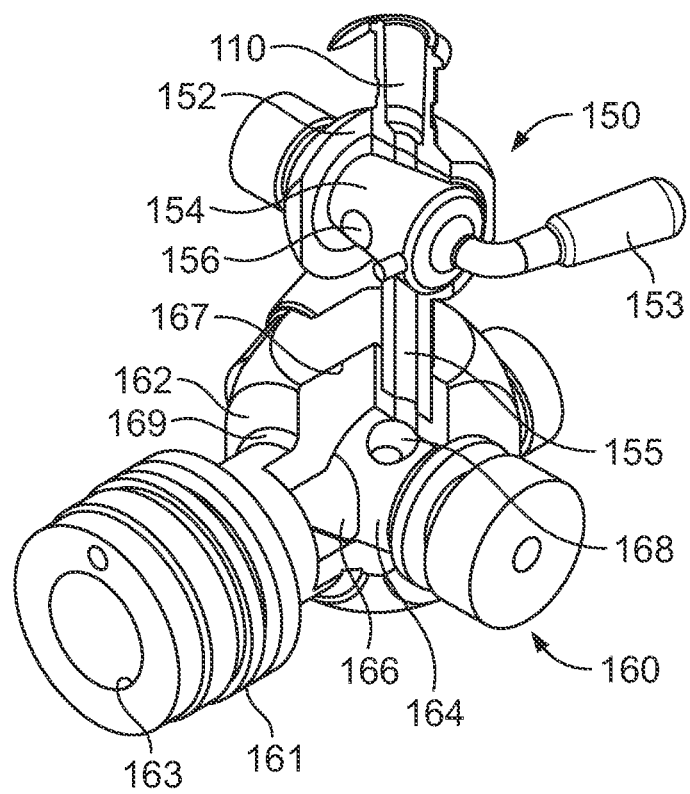
FIG. 8A is a perspective cut-away view of the primary and secondary valves of the hysteroscope of FIG. 2B, with the primary valve closed and the secondary valve in the second position.
Figure 8B:
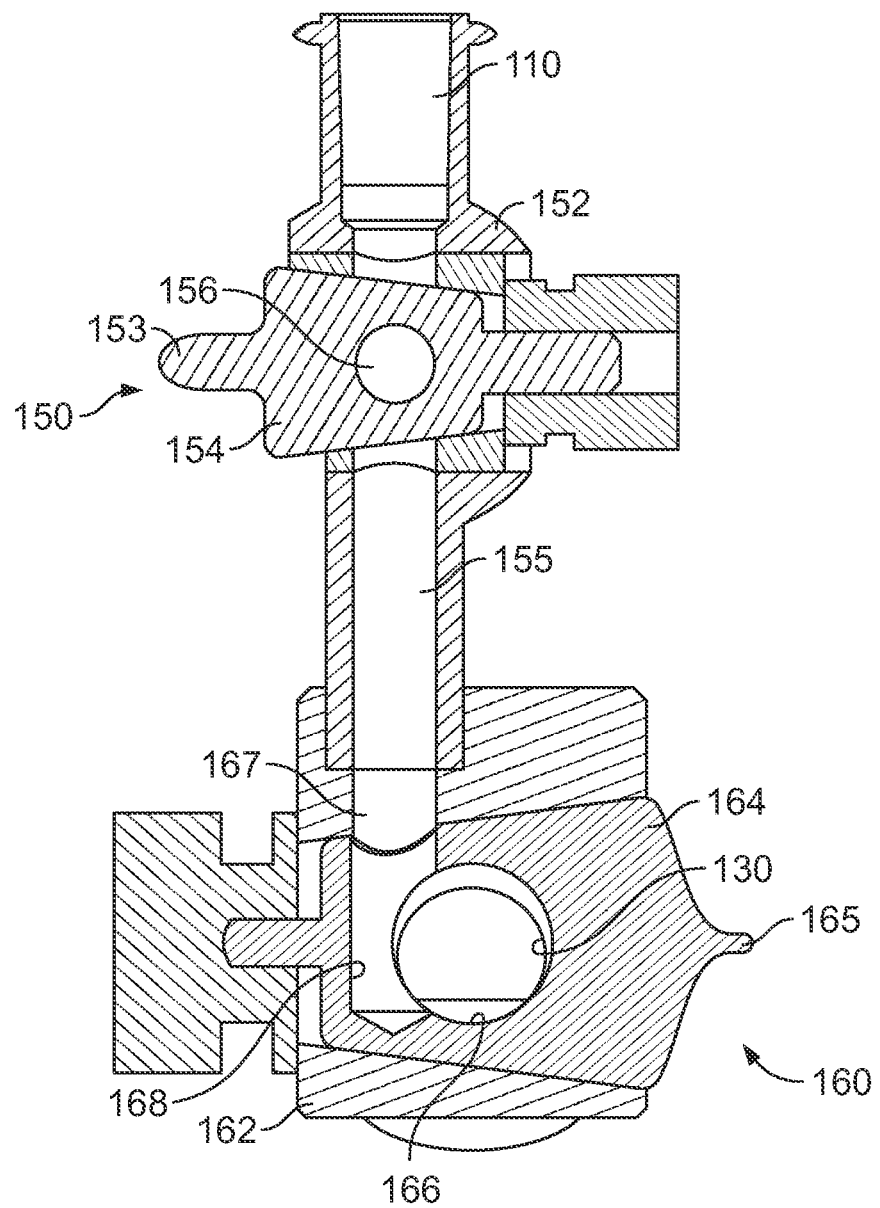
FIG. 8B is a cross-sectional view of the primary and secondary valves as shown in FIG. 8A taken along line 8B-8B.

Referring also to FIGS. 8A and 8B, a primary valve 150 is positioned between inflow port 110 and secondary valve 160 to provide on/off control of fluid flow from inflow port 110 through secondary valve 160 into inflow channel 130. Primary valve 150 includes a housing 152 and a body 154 rotatable within housing 152 and defining a throughbore 156. Body 154 is connected to a handle 153 for moving body 154 between a fully opened position (FIGS. 6A and 6B), wherein throughbore 156 is aligned with inflow port 110 to allow fluid to flow to inflow channel 130, and a fully closed position (FIGS. 8A and 8B), where fluid flow to inflow channel 130 is blocked. Primary valve 150 and secondary valve 160 are removably connected to a proximal end 107 of hysteroscope 100 by a threaded portion 161 having a bore 163 therethrough that is aligned with inflow channel 130.

Figure 9:
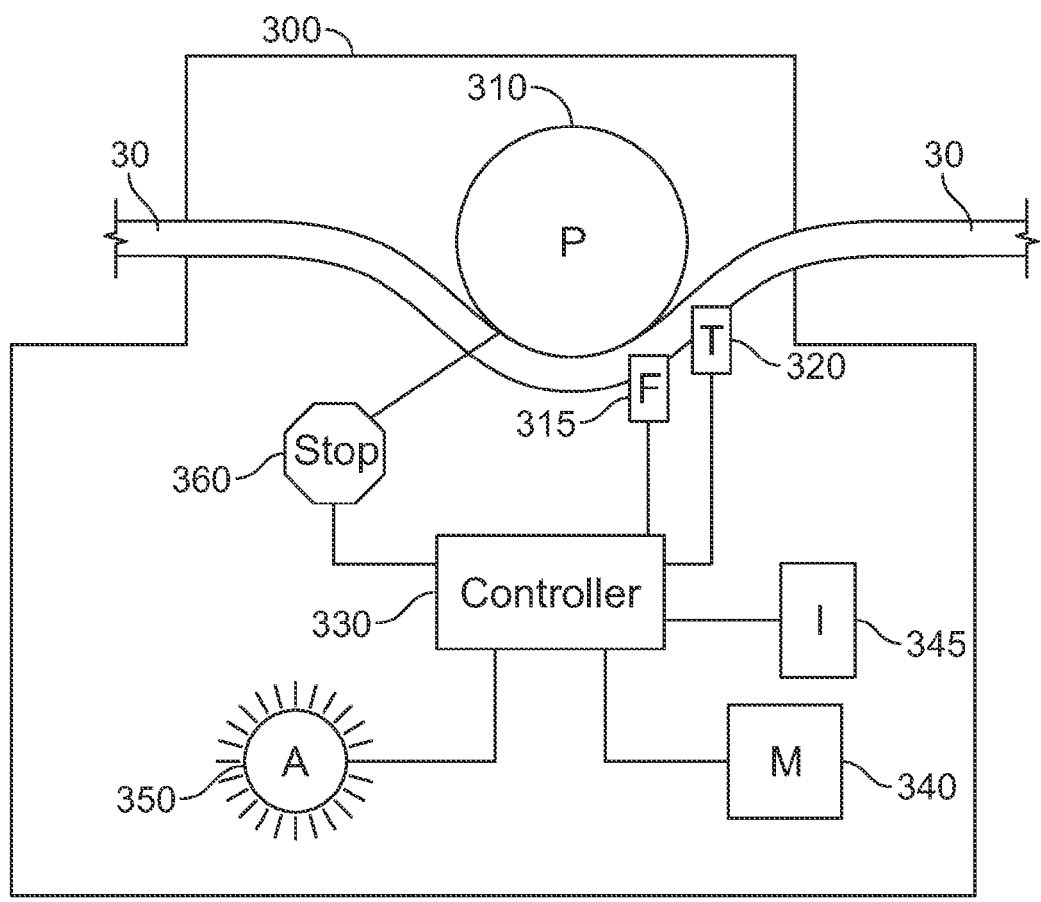
FIG. 9 is a schematic diagram of a fluid management system of the resection system of FIG. 1.

Fluid management control unit 300 maintains a substantially constant fluid pressure inside the organ by pumping sufficient fluid into the organ through inflow channel 130 to balance fluid flow out of the organ through passive outflow channel 128 and from suction of fluid through suction channel 204 (when resector 200 is received in hysteroscope 100). Referring to FIG. 9, fluid management control unit 300 includes peristaltic pump 310 through which runs fluid line 30 that transmits fluid from fluid bag 17 to inflow port 110 of hysteroscope 100. Pump 310 pumps fluid along fluid line 310, controlling the pressure and flow rate of fluid transmitted to hysteroscope 100.

Fluid management control unit 300 includes a flow rate sensor 315, such as a roller head, a turbine, or an ultrasonic sensor, that measures the flow rate of fluid outputted by pump 310. Control unit 300 also includes a pressure sensor, e.g., pressure transducer 320, that senses the fluid pressure in fluid line 30 after the fluid passes through pump 310. Fluid management control unit 300 also includes an input 345 where a user can input a desired pressure to be maintained inside the organ, and a memory 340 that contains information on the impedance (i.e., pressure drop) through the hysteroscope 100 and resector 200 combination at a range of different flow rates.

Coupled to pressure sensor 320, pump 310, flow rate sensor 315, input 345, and memory 340, is a controller 330, e.g., a microprocessor, that controls the pressure and the flow rate outputted by pump 310 based on the flow rate measured by flow rate sensor 315, the pressure measured by pressure sensor 320, the information stored in memory 340, and the target pressure 345. Based on a measured flow rate and a measured pressure, controller 330 determines the actual pressure in the organ according to the information stored in memory 340 that accounts for the impedance (i.e., pressure drop) through the hysteroscope 100 at various flow rates. Controller 330 then compares the pressure in the organ with the target pressure and adjusts the pressure and flow rate outputted by pump 310 accordingly. If the target pressure is greater than the actual pressure, then controller 330 increases the output of pump 310. If the target pressure is less than the actual pressure, then controller 330 decreases the output of pump 310.

The size and configuration of inflow channel 130, passive outflow channel 128, and suction channel 204 facilitate controller 330 maintaining substantially constant pressure in the organ. In addition, secondary valve 160 facilitates maintaining a substantially constant pressure in the organ by keeping the impedance through hysteroscope 100 the same regardless of whether resector 200 is received in hysteroscope 100. Thus, it is not necessary for controller 330 to "know" whether resector 200 is positioned in hysteroscope 100. Fluid management control unit 300 is able to maintain a relatively constant pressure of fluid within the organ, e.g., at a preset pressure between about 60 mm Hg and about 120 mm Hg.

Fluid management control unit 300 also includes a feature that verifies that a correct combination of hysteroscope 100 and resector 200 is being used (i.e., to ensure that the system is only used when a resector and a hysteroscope having properly balanced flow channels are attached to fluid management control unit 300). Memory 340 contains flow rate and impedance information for each valid combination of a hysteroscope and a resector. Controller 330 is programmed to determine whether the pressure measured by pressure transducer 320 is within a threshold value of a predetermined pressure for a given flow rate in order to verify the identity of the combination of the hysteroscope and the resector. Controller 330 is coupled to a shut-off circuit 360 to disable pump 310 when controller 330 determines that the combination of hysteroscope and resector is invalid (e.g., when an incorrect size resector is used with the hysteroscope). If the combination is verified, then controller 330 overrides shut-off circuit 360 and allows pump 310 to pump fluid to hysteroscope 100, as described above. On the other hand, if controller 330 determines that the combination of the hysteroscope and the resector is invalid (e.g., wrong size resector), the controller 330 activates shut-off circuit 360 to disable pump 310. Controller 330 also is coupled to an alarm 350, e.g., a visual or audible alarm, that is activated when pump 310 is disabled. Controller 330 is programmed to make pressure comparisons at several (e.g., three or four) flow rates prior to use of hysteroscope 100 and resector 200.

In use, a user assembles the components of resection system 10 as shown in FIG. 1. As shown in FIGS. 7A and 7B, the user positions primary valve 150 in the open position and secondary valve 160 in the second position. The user inserts resector 200 through hysteroscope 100. The user verifies the combination of hysteroscope 100 and resector 200 by activating fluid management control unit 300, as described above with respect to FIG. 9, to infuse fluid through hysteroscope 100 and resector 200 assembly at three or four different flow rates, to sense the flow impedance through the assembly, and to compare each sensed flow impedance to predetermined flow impedances. If the combination is verified, the user removes resector 200 from hysteroscope 100, closes primary valve 150, and moves secondary valve 160 to the first position, as shown in FIGS. 8A and 8B.

Figure 10:
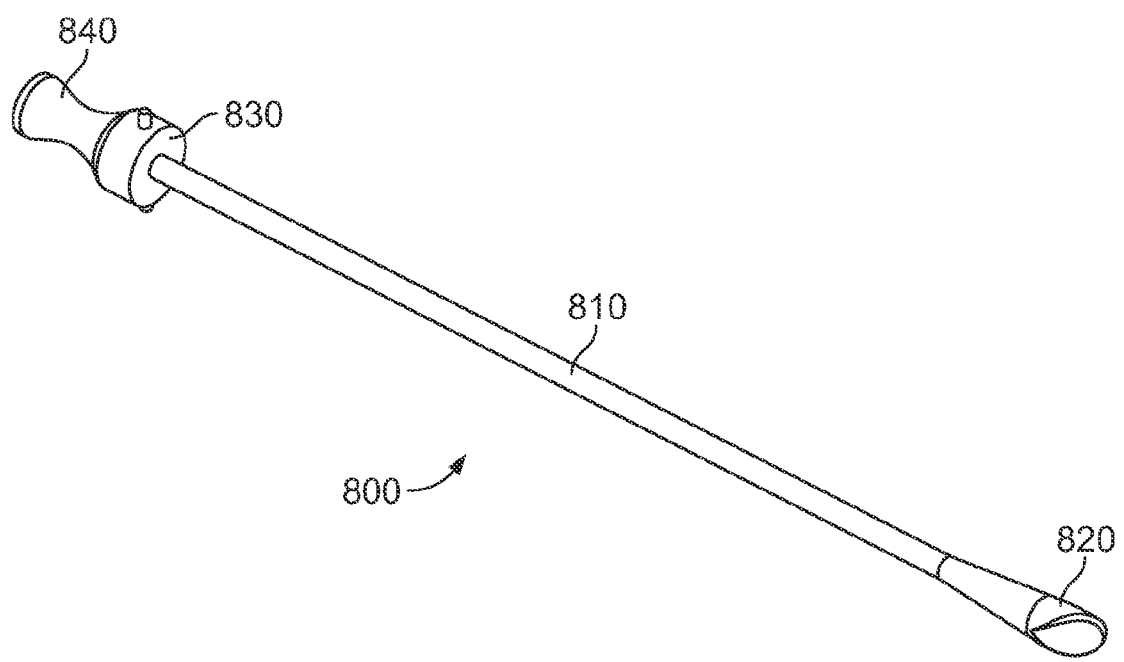
FIG. 10 is a perspective view of an obturator for use with a sheath of the hysteroscope of FIG. 2A.

Referring to FIG. 10, to position sheath 80 within the uterus, system 10 includes an obturator 800 insertable through sheath 80 when scope housing 90 is removed from sheath 80. Obturator 800 includes a shaft 810, a sharp, distal tip 820, and a proximal handle 840. Disposed between handle 840 and shaft 810 is a pin 830 that fits into the J-shaped slot (not shown) in sheath 80 to removably lock obturator 800 to sheath 80.

Figure 11:
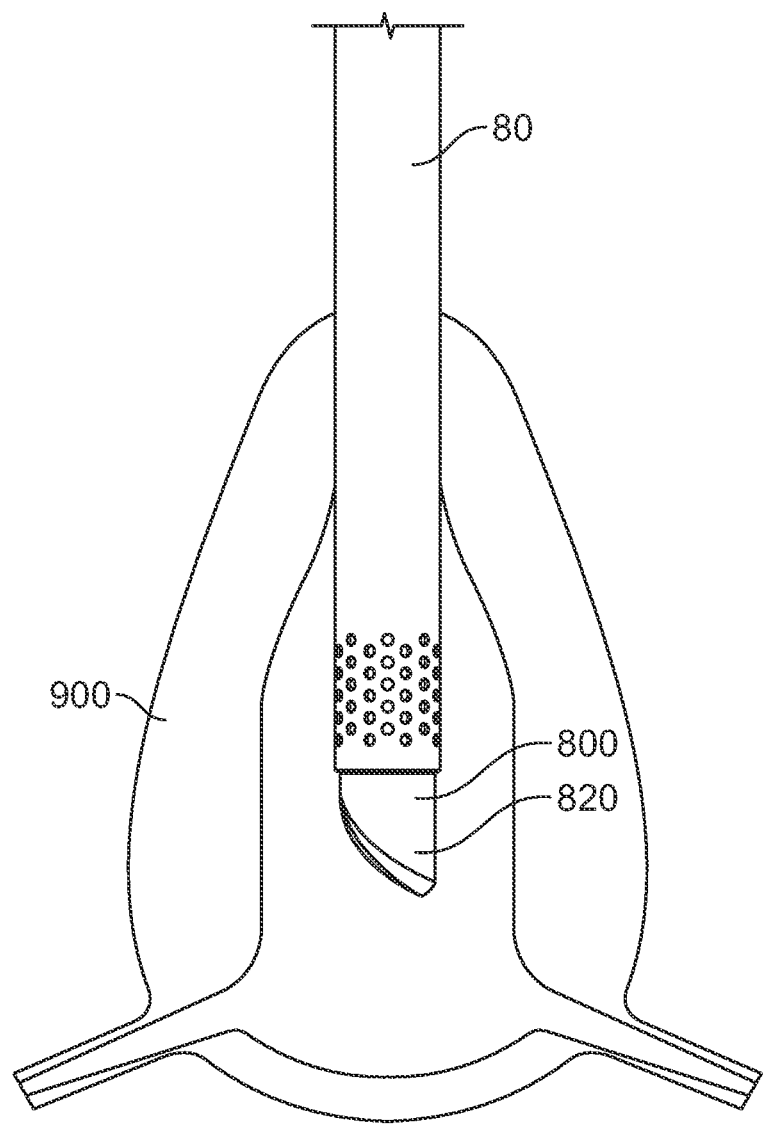
FIGS. 11-13 show the obturator, hysteroscope and resector in use.
Figure 12:
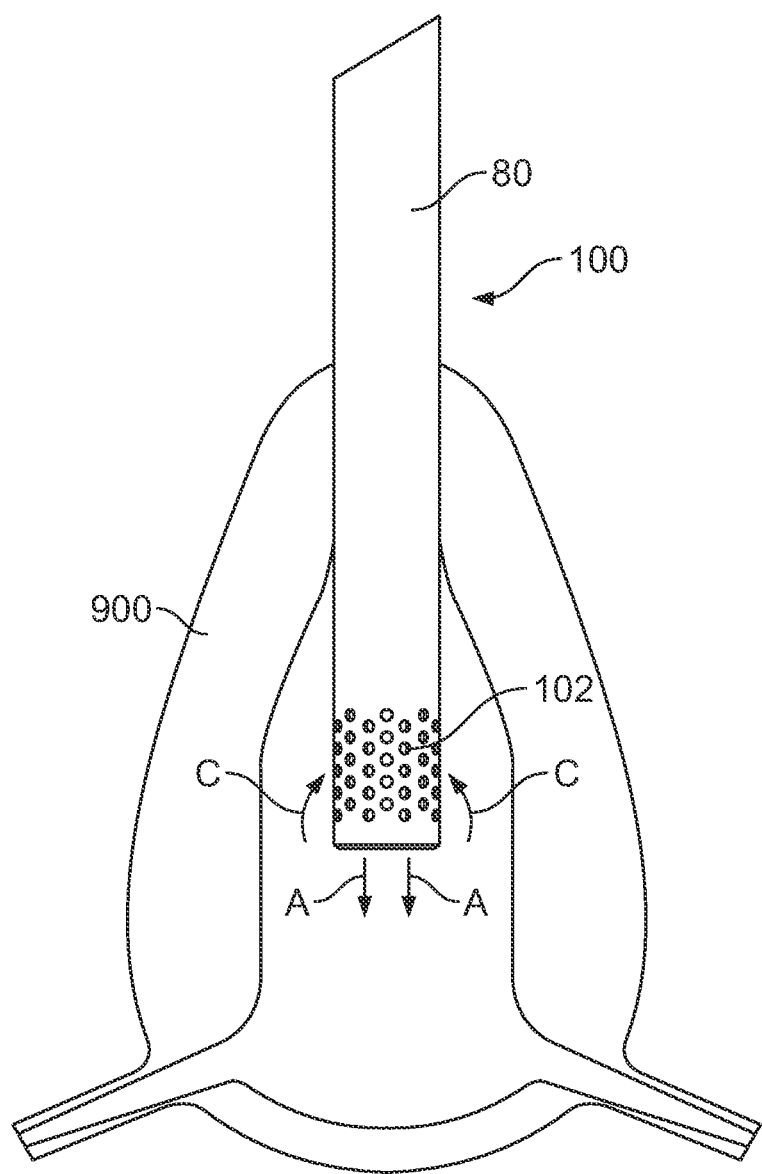

Referring to FIG. 11, with obturator 800 received within sheath 80 such that tip 820 extends beyond distal portion 102 of sheath 80, the user inserts obturator 800 and sheath 80 into a uterus 900. Referring to FIG. 12, the user removes obturator 800 from sheath 80, and inserts scope housing 90 through sheath 80 and into uterus 900. The user then opens primary valve 150 while leaving secondary valve 160 in the first position, as shown in FIGS. 6A and 6B, and activates fluid management control system 300 to pump fluid through channel 130 of hysteroscope 100 and into uterus 900 along flow path A, at a first impedance, to distend uterus 900, as shown in FIG. 12. At the same time, the user allows fluid to flow out of uterus 900 via holes 112 and channel 122 in hysteroscope 100 along flow path C to gravity container 40, in order to keep the pressure inside uterus 900 between about 60 mm Hg and 120 mm Hg.

Figure 13:
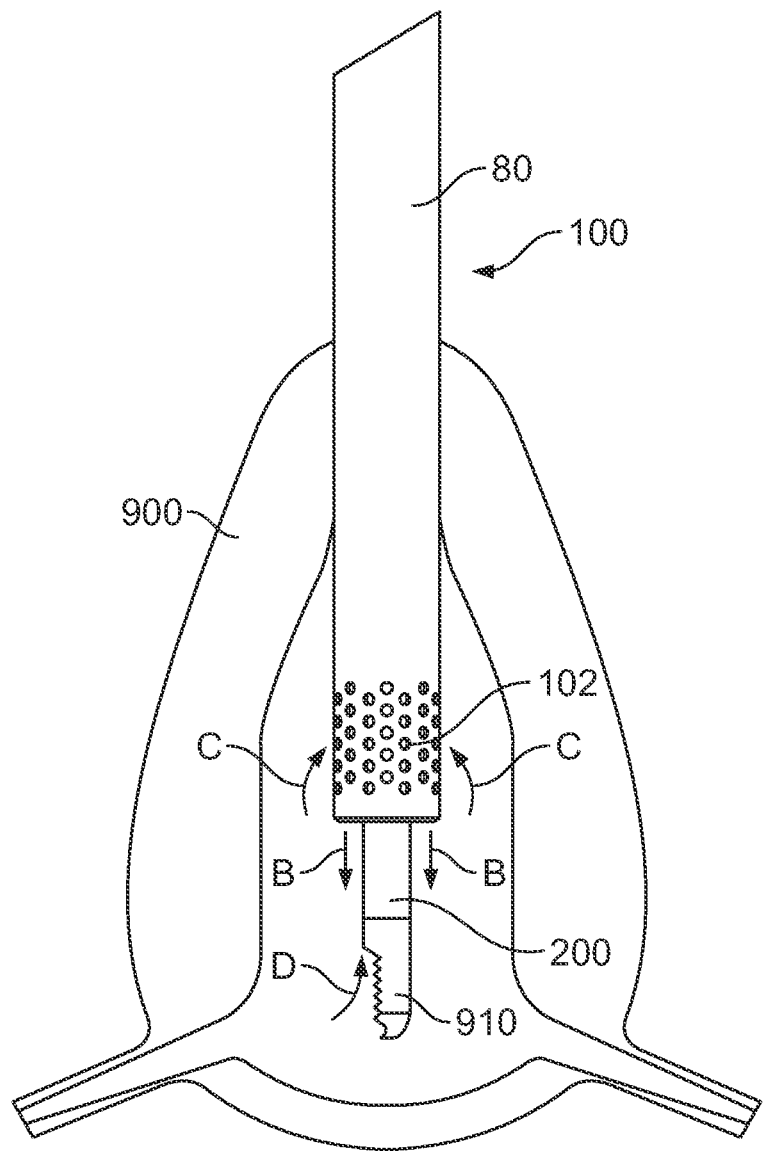

Once uterus 900 has been distended, with primary valve 150 still open, the user positions secondary valve 160 in the second position, as shown in FIGS. 7A and 7B, and inserts resector 200 through secondary valve 160 and inflow channel 130 of hysteroscope 100, and into uterus 900, as shown in FIG. 13. Fluid management control system 300 continues to pump fluid so that fluid flows through inflow channel 130, between inner wall 125 and resector 200 and into uterus 900 at a second impedance substantially equal to the first impedance. At the same time, the user allows fluid to flow out of uterus 900 via holes 112 and channel 128 in hysteroscope along flow path C and suctions fluid out of uterus 900 through resector 200 along flow path D, in order to keep the pressure inside uterus 900 between about 60 mm Hg and 120 mm Hg. Fluid suctioned along path D is collected in vacuum containers 42. The user also can actuate vacuum regulator 400 to control the amount of suction through resector 200 along path D. Preferably, the user maintains the vacuum pressure above approximately 100 mm Hg (to facilitate tissue removal) and below approximately 200 mm Hg (to inhibit uterus collapse). In order to inhibit uterus collapse, vacuum regulator 400 is preset to not allow vacuum pressure greater than a threshold value, e.g., 200 mm Hg, to be applied.

The user visualizes the inside of uterus 900 on monitors 62 of visualizing and imaging assembly 50. The user actuates foot pedal 62, which activates resector control unit 60. Resector control unit 60 activates resector 200, e.g., by rotating a cutting blade 910 at working end 220 of resector 200, to cut tissue from uterus 900. Fluid and tissue cut by blade 910 are suctioned through channel 204 of resector 200 along path D. During the procedure, resector 200 can be removed from hysteroscope 100 while hysteroscope 100 remains inside uterus 900, e.g., to clean resector 200 or change instruments, so long as the user moves secondary valve 160 to the closed position, as shown in FIGS. 6A and 6B, while removing resector 200 to permit greater inflow through channel 130 of hysteroscope 100.

During the procedure fluid monitor unit 18 tracks the amount of fluid infused through resector 200 and the amount of fluid collected in gravity container 40 and vacuum containers 42. Fluid monitor unit 18 sets off an audible or a visual alarm if substantially more fluid is infused than collected, which indicates that the patient is absorbing too much fluid. Once the procedure is complete, the user closes primary valve 150, as shown in FIGS. 8A and 8B, and removes resector 200 and hysteroscope 100 from uterus 900.

A number of embodiments of the invention have been described. Nevertheless, it will be understood that various modifications may be made without departing from the spirit and scope of the invention. For example, the shape, size, and configuration of the fluid flow channels through the hysteroscope and the resector could be different than that shown and described, such as having an inflow channel with an elliptical, square, triangular, or trapezoidal cross-section. Instead of a blind bore, the body of the secondary valve could include a peripheral channel formed in an outer surface of the body. Instead of a secondary valve, the primary valve could be electronically controlled to maintain a constant impedance through the hysteroscope regardless of whether the resector is inserted through the hysteroscope. The hysteroscope can be used with other types of resector tools having rotatable working ends, such as burrs or drills. The hysteroscope also can be used with a resector tool having a reciprocating working end, such as the instrument disclosed in U.S. patent application Ser. No. 10/318,400 entitled "Reciprocating rotary arthroscopic surgical instrument," the entirety of which is incorporated herein by reference. The fluid management system can include another type of pump, such as a centrifugal, piston, or diaphragm pump. The vacuum regulator could include a manually or electronically operable valve, a flow sensor, and/or a pressure gauge. The devices shown can be used for surgery on other distensible organs, such as a shoulder or knee joint. Different combinations of the components of the system could be used or components could be added or deleted. These and other embodiments are within the scope of the following claims.

What is claimed is:

1. A surgical system comprising: a first instrument defining a fluid flow channel; a second instrument receivable by the first instrument fluid flow channel; and a valve coupled to the first instrument fluid flow channel to control fluid flow through the first instrument fluid flow channel; wherein the valve includes a housing and a body moveable within the housing, the body defining an opening and being moveable within the housing between a first position in which the opening is not aligned with the first instrument fluid flow channel, and a second position in which the opening is aligned with the first instrument fluid flow channel, and wherein the opening provides a first predefined impedance to fluid flow through the valve when the body is in the first position and the opening provides a second predefined impedance to fluid flow through the valve when the body is in the second position, and wherein fluid is permitted to flow through the opening defined by the body of the valve to and through the first instrument fluid flow channel when the body is in the first position and when the body is in the second position.

2. The surgical system according to claim 1 wherein the impedance to fluid flow through the valve and the first instrument fluid flow channel when the body is in the first position is substantially equal to the impedance to fluid flow through the valve and the first instrument fluid flow channel when the body is in the second position and when the second instrument is received in the first instrument fluid flow channel.

3. The surgical system according to claim 1 wherein the second predefined impedance to fluid flow through the valve when the body is in the second position is less than the first predefined impedance to fluid flow through the valve when the body is in the first position.

4. The surgical system of claim 1 wherein the first instrument includes an outer member and an inner member, the inner member defining the first instrument fluid flow channel therethrough, the inner member being received within the outer member, and the outer member and the inner member defining a second fluid flow channel therebetween.

5. The surgical system of claim 4 wherein the second instrument includes a tube defining a second instrument channel therethrough, the tube partially blocking the first instrument fluid flow channel when received therein.

6. The surgical system of claim 5 wherein the second fluid flow channel has a cross-sectional area of about 0.0083 to about 0.0249 square inches, the first instrument fluid flow channel has a cross-sectional area of about 0.0053 to about 0.0159 square inches, and the second instrument channel has a cross-sectional area of about 0.0042 to about 0.013 square inches.

7. The surgical system of claim 6 wherein the second fluid flow channel has a cross-sectional area of about 0.0166 square inches, the first instrument fluid flow channel has a cross-sectional area of about 0.0106 square inches, and the second instrument channel has a cross-sectional area of about 0.0085 square inches.

8. The surgical system of claim 1 further comprising a pump coupled to the first instrument such that the pump is configured to infuse fluid through the first instrument fluid flow channel.

9. The surgical system of claim 8 wherein the pump is programmed to infuse fluid through the first instrument fluid flow channel to maintain a substantially constant pressure of between about 60 mm Hg and about 120 mm Hg inside a distensible organ.

10. The surgical system of claim 8 further comprising a sensor coupled to the pump to sense a flow impedance at a given flow rate and a controller coupled to the sensor and the pump to compare the sensed flow impedance to a predetermined flow impedance for the given flow rate to verify the identity of the first and second instruments.

11. The surgical system of claim 1 wherein the second instrument has a channel in fluid communication with a source of suction and further comprising a regulator interposed between the second instrument channel and the source of suction to regulate an amount of suction applied through the second instrument channel.

12. A surgical system comprising: a first instrument defining a fluid flow channel; a second instrument receivable by the first instrument fluid flow channel; and impedance means for maintaining a constant and finite impedance to fluid flow through the first instrument fluid flow channel with and without the second instrument received in the first instrument fluid flow channel; wherein the impedance means includes a housing and a body moveable within the housing, the body defining an opening and being moveable within the housing between a first position in which the opening is not aligned with the first instrument fluid flow channel, and a second position in which the opening is aligned with the first instrument fluid flow channel, and wherein the opening provides a first predefined impedance to fluid flow through the impedance means when the body is in the first position and the opening provides a second predefined impedance to fluid flow through the impedance means when the body is in the second position, and wherein fluid is permitted to flow through the opening defined by the body of the impedance means to and through the first instrument fluid flow channel when the body is in the first position and when the body is in the second position.

13. The surgical system according to claim 12 wherein the impedance to fluid flow through the impedance means and the first instrument fluid flow channel when the body is in the first position is substantially equal to the impedance to fluid flow through the body and the first instrument fluid flow channel when the body is in the second position and when the second instrument is received in the first instrument fluid flow channel.

14. The surgical system according to claim 12 wherein the second predefined impedance to fluid flow through the impedance means when the body is in the second position is less than the first predefined impedance to fluid flow through the impedance means when the body is in the first position.

15. The surgical system of claim 12 wherein the first instrument includes an outer member and an inner member, the inner member defining the first instrument fluid flow channel therethrough, the inner member being received within the outer member, and the outer member and the inner member defining a second fluid flow channel therebetween.

16. The surgical system of claim 15 wherein the second instrument includes a tube defining a second instrument channel therethrough, the tube partially blocking the first instrument fluid flow channel when received therein.

17. The surgical system of claim 16 wherein the second fluid flow channel has a cross-sectional area of about 0.0083 to about 0.0249 square inches, the first instrument fluid flow channel has a cross-sectional area of about 0.0053 to about 0.0159 square inches, and the second instrument channel has a cross-sectional area of about 0.0042 to about 0.013 square inches.

18. The surgical system of claim 17 wherein the second fluid flow channel has a cross-sectional area of about 0.0166 square inches, the first instrument fluid flow channel has a cross-sectional area of about 0.0106 square inches, and the second instrument channel has a cross-sectional area of about 0.0085 square inches.

19. The surgical system of claim 12 further comprising a pump coupled to the first instrument such that the pump is configured to infuse fluid through the first instrument fluid flow channel.

20. The surgical system of claim 19 wherein the pump is programmed to infuse fluid through the first instrument fluid flow channel to maintain a substantially constant pressure of between about 60 mm Hg and about 120 mm Hg inside a distensible organ.

21. The surgical system of claim 19 further comprising a sensor coupled to the pump to sense a flow impedance at a given flow rate and a controller coupled to the sensor and the pump to compare the sensed flow impedance to a predetermined flow impedance for the given flow rate to verify the identity of the first and second instruments.

22. The surgical system of claim 12 wherein the second instrument has a channel in fluid communication with a source of suction and further comprising a regulator interposed between the second instrument channel and the source of suction to regulate an amount of suction applied through the second instrument channel.

23. A surgical system comprising:
a first instrument defining a fluid flow channel;
a second instrument receivable by the first instrument fluid flow channel; and
a valve coupled to the first instrument fluid flow channel to control fluid flow through the first instrument fluid flow channel;
wherein the valve includes a housing and a body moveable within the housing, the body defining a first body channel and a second body channel and being moveable within the housing between a first position in which the second body channel is not aligned with the first instrument fluid flow channel, and a second position in which the second body channel is aligned with the first instrument fluid flow channel, and
wherein the impedance to fluid flow through the valve and the first instrument fluid flow channel when the body is in the second position and the second instrument is not received in the first instrument fluid flow channel is less than the impedance to fluid flow through the valve and the first instrument fluid flow channel when the body is in the first position and the second instrument is not received in the first instrument fluid flow channel, and
wherein fluid is permitted to flow through the first and second body channels defined by the body of the valve to and through the first instrument fluid flow channel when the body is in the first position and when the body is in the second position.

24. The surgical system according to claim 13 wherein the impedance to fluid flow through the valve and the first instrument fluid flow channel when the body is in the first position and the second instrument is not received in the first instrument fluid flow channel is substantially equal to the impedance to fluid flow through the valve and the first instrument fluid flow channel when the body is in the second position and the second instrument is received in the first instrument fluid flow channel.

25. The surgical system of claim 13 wherein the first instrument includes an outer member and an inner member, the inner member defining the first instrument fluid flow channel therethrough, the inner member being received within the outer member, and the outer member and the inner member defining a second fluid flow channel therebetween.

26. The surgical system of claim 25 wherein the second instrument includes a tube defining a second instrument channel therethrough, the tube partially blocking the first instrument fluid flow channel when received therein.

27. The surgical system of claim 26 wherein the second fluid flow channel has a cross-sectional area of about 0.0083 to about 0.0249 square inches, the first instrument fluid flow channel has a cross-sectional area of about 0.0053 to about 0.0159 square inches, and the second instrument channel has a cross-sectional area of about 0.0042 to about 0.013 square inches.

28. The surgical system of claim 27 wherein the second fluid flow channel has a cross-sectional area of about 0.0166 square inches, the first instrument fluid flow channel has a cross-sectional area of about 0.0106 square inches, and the second instrument channel has a cross-sectional area of about 0.0085 square inches.

29. The surgical system of claim 23 further comprising a pump coupled to the first instrument such that the pump is configured to infuse fluid through the first instrument fluid flow channel.

30. The surgical system of claim 29 wherein the pump is programmed to infuse fluid through the first instrument fluid flow channel to maintain a substantially constant pressure of between about 60 mm Hg and about 120 mm Hg inside a distensible organ.

31. The surgical system of claim 29 further comprising a sensor coupled to the pump to sense a flow impedance at a given flow rate and a controller coupled to the sensor and the pump to compare the sensed flow impedance to a predetermined flow impedance for the given flow rate to verify the identity of the first and second instruments.

32. The surgical system of claim 23 wherein the second instrument has a channel in fluid communication with a source of suction and further comprising a regulator interposed between the second instrument channel and the source of suction to regulate an amount of suction applied through the second instrument channel.

33. A surgical system comprising:
a first instrument defining a fluid flow channel;
a second instrument receivable by the first instrument fluid flow channel; and
impedance means for maintaining a constant and finite impedance to fluid flow through the first instrument fluid flow channel with and without the second instrument received in the first instrument fluid flow channel;
wherein the impedance means includes a housing and a body moveable within the housing, the body defining a first body channel and a second body channel and being moveable within the housing between a first position in which the second body channel is not aligned with the first instrument fluid flow channel, and a second position in which the second body channel is aligned with the first instrument fluid flow channel, and
wherein the impedance to fluid flow through the impedance means and the first instrument fluid flow channel when the body is in the second position and the second instrument is not received in the first instrument fluid flow channel is less than the impedance to fluid flow through the impedance means and the first instrument fluid flow channel when the body is in the first position and the second instrument is not received in the first instrument fluid flow channel, and
wherein fluid is permitted to flow through the first and second body channels defined by the body of the impedance means to and through the first instrument fluid flow channel when the body is in the first position and when the body is in the second position.

34. The surgical system according to claim 33 wherein the impedance to fluid flow through the impedance means and the first instrument fluid flow channel when the body is in the first position and the second instrument is not received in the first instrument fluid flow channel is substantially equal to the impedance to fluid flow through the impedance means and the first instrument fluid flow channel when the body is in the second position and the second instrument is received in the first instrument fluid flow channel.

35. The surgical system of claim 33 wherein the first instrument includes an outer member and an inner member, the inner member defining the first instrument fluid flow channel therethrough, the inner member being received within the outer member, and the outer member and the inner member defining a second fluid flow channel therebetween.

36. The surgical system of claim 35 wherein the second instrument includes a tube defining a second instrument channel therethrough, the tube partially blocking the first instrument fluid flow channel when received therein.

37. The surgical system of claim 36 wherein the second fluid flow channel has a cross-sectional area of about 0.0083 to about 0.0249 square inches, the first instrument fluid flow channel has a cross-sectional area of about 0.0053 to about 0.0159 square inches, and the second instrument channel has a cross-sectional area of about 0.0042 to about 0.013 square inches.

38. The surgical system of claim 37 wherein the second fluid flow channel has a cross-sectional area of about 0.0166 square inches, the first instrument fluid flow channel has a cross-sectional area of about 0.0106 square inches, and the second instrument channel has a cross-sectional area of about 0.0085 square inches.

39. The surgical system of claim 33 further comprising a pump coupled to the first instrument such that the pump is configured to infuse fluid through the first instrument fluid flow channel.

40. The surgical system of claim 39 wherein the pump is programmed to infuse fluid through the first instrument fluid flow channel to maintain a substantially constant pressure of between about 60 mm Hg and about 120 mm Hg inside a distensible organ.

41. The surgical system of claim 39 further comprising a sensor coupled to the pump to sense a flow impedance at a given flow rate and a controller coupled to the sensor and the pump to compare the sensed flow impedance to a predetermined flow impedance for the given flow rate to verify the identity of the first and second instruments.

42. The surgical system of claim 33 wherein the second instrument has a channel in fluid communication with a source of suction and further comprising a regulator interposed between the second instrument channel and the source of suction to regulate an amount of suction applied through the second instrument channel.

43. A surgical system comprising: a first instrument defining a fluid flow channel; a second instrument receivable by the first instrument fluid flow channel; and a valve coupled to the first instrument fluid flow channel to control fluid flow through the first instrument fluid flow channel; wherein the valve includes a housing and a body moveable within the housing, the body defining an opening and being moveable within the housing between a first position in which the opening is not aligned with the first instrument fluid flow channel, and a second position in which the opening is aligned with the first instrument fluid flow channel, and wherein the opening provides a first predefined impedance to fluid flow through the valve when the body is in the first position and the opening provides a second predefined impedance to fluid flow through the valve when the body is in the second position, and wherein the impedance to fluid flow through the valve and the first instrument fluid flow channel when the body is in the first position and when the second instrument is not received in the first instrument fluid flow channel is substantially equal to the impedance to fluid flow through the valve and the first instrument fluid flow channel when the body is in the second position and when the second instrument is received in the first instrument fluid flow channel.

44. The surgical system according to claim 43 wherein fluid is permitted to flow through the opening defined by the body of the valve to and through the first instrument fluid flow channel when the body is in the first position and when the body is in the second position.

* * * * *